US009822378B2

(12) United States Patent
Kruse

(10) Patent No.: US 9,822,378 B2
(45) Date of Patent: Nov. 21, 2017

(54) INTRACELLULAR TRANSLATION OF CIRCULAR RNA

(71) Applicant: Robert Kruse, Houston, TX (US)

(72) Inventor: Robert Kruse, Houston, TX (US)

(73) Assignee: Ribokine, LLC, Houston, TX (US)

( * ) Notice: Subject to any disclaimer, the term of this patent is extended or adjusted under 35 U.S.C. 154(b) by 0 days.

(21) Appl. No.: 14/890,799

(22) PCT Filed: May 13, 2014

(86) PCT No.: PCT/US2014/037795
§ 371 (c)(1),
(2) Date: Nov. 12, 2015

(87) PCT Pub. No.: WO2014/186334
PCT Pub. Date: Nov. 20, 2014

(65) Prior Publication Data
US 2016/0083747 A1    Mar. 24, 2016

Related U.S. Application Data

(60) Provisional application No. 61/823,709, filed on May 15, 2013.

(51) Int. Cl.
 *C12N 15/85*   (2006.01)
 *C12N 15/115*  (2010.01)
 *C12Q 1/68*    (2006.01)
 *A61K 48/00*   (2006.01)

(52) U.S. Cl.
 CPC ............ *C12N 15/85* (2013.01); *C12N 15/115* (2013.01); *C12Q 1/6865* (2013.01); *A61K 48/00* (2013.01); *C12N 2310/16* (2013.01); *C12N 2800/50* (2013.01); *C12N 2830/42* (2013.01); *C12N 2840/203* (2013.01); *C12N 2840/44* (2013.01); *C12N 2999/007* (2013.01)

(58) Field of Classification Search
None
See application file for complete search history.

(56) References Cited

U.S. PATENT DOCUMENTS

| | | | |
|---|---|---|---|
| 5,580,859 | A | 12/1996 | Felgner |
| 5,766,903 | A | 6/1998 | Sarnow |
| 5,773,244 | A | 6/1998 | Ares |
| 5,824,497 | A | 10/1998 | Andrews |
| 6,210,931 | B1 | 4/2001 | Feldstein |
| 8,192,984 | B2 | 6/2012 | Atabekov |
| 8,257,945 | B2 | 9/2012 | Atabekov |
| 8,278,036 | B2 | 10/2012 | Kariko |
| 2009/0170800 | A1 | 7/2009 | Wiener |
| 2009/0203765 | A1 | 8/2009 | Bhanot |
| 2009/0286852 | A1 | 11/2009 | Kariko |
| 2010/0047261 | A1 | 2/2010 | Hoerr |
| 2010/0137407 | A1 | 6/2010 | Abe |
| 2011/0104127 | A1 | 5/2011 | Torzewski |
| 2011/0143397 | A1 | 6/2011 | Kariko |
| 2012/0251618 | A1 | 10/2012 | Schrum |

FOREIGN PATENT DOCUMENTS

| | | |
|---|---|---|
| JP | 2004344008 | 12/2004 |
| WO | 0155371 | 8/2001 |
| WO | 03048306 | 6/2003 |
| WO | 2005102041 | 11/2005 |
| WO | 2007044627 | 4/2007 |
| WO | 2010084371 | 7/2010 |
| WO | 2012170433 | 12/2012 |

OTHER PUBLICATIONS

Chen C.Y. & Sarnow P., Initiation of Protein Synthesis by the Eukaryotic Translational Apparatus on Circular RNAs. Science, New Series, 268(5209): 415-417 (1995).
Wang, G., et al., Cap-independent translation of human SP-A 5'-UTR variants: a double-loop structure and cis-element contribution, Am J Physiol Lung Cell Mol Physiol296:L635-L647 (2009).
Perriman & Ares, Circular mRNA can direct translation of extremely long repeating-sequence proteins in vivo. RNA (1998)4:1047-1054.
Perriman, R. Circular mRNA Encoding for Monomeric and Polymeric Green Fluorescent Protein. Methods in Molecular Biology 183:69-85 (2002).
Van Lieshout, J.F.T., et al., Ribozyme-mediated engineering of circular 25 mRNA and its functional in vivo and in vitro translation, Chapter 7, (2007). available at: http://citeseerx.ist.psu.edu/viewdoc/download?doi=10.1.1.98.189&rep=rep1&type=pdf#page=117.
Wang Z., et al., The cap-binding translation initiation factor, eIF4E, binds a pseudoknot in a viral cap-independent translation element. Structure19(6):868-80 (2011).
Mochizuki K., et al., High affinity RNA for mammalian initiation factor 4E interferes with mRNA-cap binding and inhibits translation, RNA 11: 77-89 (2005).
Culjkovic B., et al., eIF4E promotes nuclear export of cyclin D1 mRNAs 15 via an element in the 3' UTR., Journal of Cell Biology 169(2): 245-256 (2005).
De Gregorio E., et al., Tethered-function analysis reveals that eIF4E can recruit ribosomes independent of its binding to the cap structure. RNA 7:106-113 (2001 ).
Umekage et al. "In Vivo Circular RNA Expression by the Permuted Intron-Exon Method," 18—Innovations in Biotechnology, Feb. 17, 2012 (Feb. 17, 2012).

(Continued)

*Primary Examiner* — Antonio Galisteo Gonzalez
(74) *Attorney, Agent, or Firm* — Boulware & Valoir

(57) ABSTRACT

A circular mRNA molecule possessing features resembling native mammalian mRNA demonstrates improved translation, while retaining the properties of an extremely long half-life inside cells. This circular mRNA is functional inside mammalian cells, being able to compete against native cellular mRNAs for the eukaryotic translation initiation machinery. The invention possesses additional RNA elements compared to a previous invention containing only an IRES element for successful in vitro or in vivo translation.

17 Claims, 9 Drawing Sheets

(56) References Cited

OTHER PUBLICATIONS

Valdmanis et al. "The Expanding Repertoire of Circular RNAs" Molecular Therapy, Jun. 6, 2013, vol. 21, No. 6, pp. 1112-1114.
International Search Report for PCT/2014/037795, dated Oct. 17, 2014.
Umekage, S. & Kikuchi Y., In vitro and in vivo production and purification of circular RNA aptamer. Journal of Biotechnology 139: 265-272 (2009).
European Search Report for counterpart application, 14797117.0, dated Dec. 23, 2016.

FIGURE 4

| | |
|---|---|
| SEQ ID NO. 1: T7 RNA Polymerase Promoter – 21 bp | TAATACGACT CACTATAGGGC |
| SEQ ID NO. 2: 5' Group I Intron sequence – 167 bp | GGTTCTACAT AAAGCCTAAC GATATCCCTT TGGGAGTAGG TCAAGTGACC GAAACGATGA CAACTTGTTT AACAAGTGGA GATATGTCTG CTCTCATGGT GACTGCAGCT GGTATAATTC CGGGTAAGAT AACGACCTTT CTGAACATAA TGCTACCGTT TAATATT |
| SEQ ID NO. 3: eIF4E aptamer 1 sequence – 86 bp | GGGAGACAAG AAUAAACGCU CAAUGUUCAA CCAGAGUGAA ACCACUAACG GGUCAGAGCC CCUUCGACAG GAGGCUCACA ACAGGC |
| SEQ ID NO. 4: Human Beta Globin 5' UTR – 50 bp | ACATTTGCTT CTGACACAAC TGTGTTCACT AGCAACCTCA AACAGACACC |
| SEQ ID NO. 5: Human Beta Globin 3' UTR – 133 bp | AGCTCGCTTT CTTGCTGTCC AATTTCTATT AAAGGTTCCT TTGTTCCCTA AGTCCAACTA CTAAACTGGG GGATATTATG AAGGGCCTTG AGCATCTGGA TTCTGCCTAA TAAAAAACAT TTATTTTCAT TGC |
| SEQ ID NO. 6: 3' Group I Intron sequence – 107 bp | ATGTTTTCTT GGGTTAATTG AGGCCTGAGT ATAAGGTGAC TTATACTTGT AATCTATCTA AACGGGGAAC CTCTCTAGTA GACAATCCCG TGCTAAATTG TAGGACT |
| SEQ ID NO. 7: T7 RNA Polymerase Terminator – 47 bp | TAGCATAACC CCTTGGGGCC TCTAAACGGG TCTTGAGGGG TTTTTTT |
| SEQ ID NO. 8: Polyadenylation Sequence – 33 bp | AAAAAAAAAA AAAAAAAAAA AAAAAAAAAA AAA |
| SEQ ID NO. 9: Encephalomyocarditis virus (EMCV) IRES – 593 bp | GGGCGGCTAT AGGGGCGGCT CGAGCGGGAT CAATTCCGCC CCCCCCCTAA CGTTACTGGC CGAAGCCGCT TGGAATAAGG CCGGTGTGCG TTTGTCTATA TGTTATTTTC CACCATATTG CGCCCGGAAA CCTGGCCCTG TCTTCTTGAC GAGCATTCCT AGGGGTCTTT CCCCTCTCGC CAAAGGAATG CAAGGTCTGT TGAATGTCGT GAAGGAAGCA GTTCCTCTGG AAGCTTCTTG AAGACAAACA ACGTCTGTAG CGACCCTTTG CAGGCAGCGG AACCCCCCAC CTGGCGACAG GTGCCTCTGC GGCCAAAAGC CACGTGTATA AGATACACCT GCAAAGGCGG CACAACCCCA GTGCCACGTT GTGAGTTGGA TAGTTGTGGA AAGAGTCAAA TGGCTCTCCT CAAGCGTATT CAACAAGGGG CTGAAGGATG CCCAGAAGGT ACCCCATTGT ATGGGATCTG ATCTGGGGCC TCGGTGCACA TGCTTTACAT GTGTTTAGTC GAGGTTAAAA AAACGTCTAG GCCCCCCGAA CCACGGGGAC GTGGTTTTCC TTTGAAAAAC ACGATGATAA TATGGCCACA ACC |

FIGURE 5

| pBSK-CR Outline: HindIII site – T7 promoter – BamHI site – 5' Group I Intron circularization sequence – XhoI site – eIF4E aptamer – SacI site – 5' UTR globin – NcoI site – linker region – SalI site – 3' UTR beta globin – polyA tail – XbaI site – 3' Group I intron circularization sequence – ClaI site – T7 terminator - HindIII site |
|---|
| SEQ ID NO. 10: pBSK-CR sequence = synthesized DNA sequence based on outline above. Genes of Interest can be cloned between NcoI and SalI and expressed as a circular mRNA with eIF4E aptamer – 5'UTR beta globin – GOI – 3'UTR beta globin – polyA. |
| AAGCTTTAAT ACGACTCACT ATAGGGCGGA TCCGGTTCTA CATAAAGCCT AACGATATCC CTTTGGGAGT AGGTCAAGTG ACCGAAACGA TGACAACTTG TTTAACAAGT GGAGATATGT CTGCTCTCAT GGTGACTGCA GCTGGTATAA TTCCGGGTAA GATAACGACC TTTCTGAACA TAATGCTACC GTTTAATATT CTCGAGGGGA GACAAGAATA AACGCTCAAT GTTCAACCAG AGTGAAACCA CTAACGGGTC AGAGCCCCTT CGACAGGAGG CTCACAACAG GCGAGCTCAC ATTTGCTTCT GACACAACTG TGTTCACTAG CAACCTCAAA CAGACACCAT GGTGCATCTG ACTCCTGAGT CGACGCTCGC TTTCTTGCTG TCCAATTTCT ATTAAAGGTT CCTTTGTTCC CTAAGTCCAA CTACTAAACT GGGGGATATT ATGAAGGGCC TTGAGCATCT GGATTCTGCC TAAAAAAAAA AAAAAAAAAA AAAAAAAAAA AAAATCTAGA ATGTTTTCTT GGGTTAATTG AGGCCTGAGT ATAAGGTGAC TTATACTTGT AATCTATCTA AACGGGGAAC CTCTCTAGTA GACAATCCCG TGCTAAATTG TAGGACTATC GATTCGTAGC ATAACCCCTT GGGGCCTCTA AACGGGTCTT GAGGGGTTTT TTTAAGCTT |

FIGURE 6

| SEQ ID NO. 11: Gene 1LG – Expresses uncapped Linear mRNA containing IRES-GFP |
|---|
| AAGCTTTAAT ACGACTCACT ATAGGGCGGA TCCGGGGCGG CTATAGGGGC GGCTCGAGCG |
| GGATCAATTC CGCCCCCCCC CTAACGTTAC TGGCCGAAGC CGCTTGGAAT AAGGCCGGTG |
| TGCGTTTGTC TATATGTTAT TTTCCACCAT ATTGCGCCCG GAAACCTGGC CCTGTCTTCT |
| TGACGAGCAT TCCTAGGGGT CTTTCCCCTC TCGCCAAAGG AATGCAAGGT CTGTTGAATG |
| TCGTGAAGGA AGCAGTTCCT CTGGAAGCTT CTTGAAGACA AACAACGTCT GTAGCGACCC |
| TTTGCAGGCA GCGGAACCCC CCACCTGGCG ACAGGTGCCT CTGCGGCCAA AAGCCACGTG |
| TATAAGATAC ACCTGCAAAG GCGGCACAAC CCCAGTGCCA CGTTGTGAGT TGGATAGTTG |
| TGGAAAGAGT CAAATGGCTC TCCTCAAGCG TATTCAACAA GGGGCTGAAG GATGCCCAGA |
| AGGTACCCCA TTGTATGGGA TCTGATCTGG GGCCTCGGTG CACATGCTTT ACATGTGTTT |
| AGTCGAGGTT AAAAAAACGT CTAGGCCCCC CGAACCACGG GGACGTGGTT TTCCTTTGAA |
| AAACACGATG ATAATATGGC CACAACCATG GTGAGCAAGG GCGAGGAGCT GTTCACCGGG |
| GTGGTGCCCA TCCTGGTCGA GCTGGACGGC GACGTAAACG GCCACAAGTT CAGCGTGTCC |
| GGCGAGGGCG AGGGCGATGC CACCTACGGC AAGCTGACCC TGAAGTTCAT CTGCACCACC |
| GGCAAGCTGC CCGTGCCCTG GCCCACCCTC GTGACCACCC TGACCTACGG CGTGCAGTGC |
| TTCAGCCGCT ACCCCGACCA CATGAAGCAG CACGACTTCT TCAAGTCCGC CATGCCCGAA |
| GGCTACGTCC AGGAGCGCAC CATCTTCTTC AAGGACGACG GCAACTACAA GACCCGCGCC |
| GAGGTGAAGT TCGAGGGCGA CACCCTGGTG AACCGCATCG AGCTGAAGGG CATCGACTTC |
| AAGGAGGACG GCAACATCCT GGGGCACAAG CTGGAGTACA ACTACAACAG CCACAACGTC |
| TATATCATGG CCGACAAGCA GAAGAACGGC ATCAAGGTGA ACTTCAAGAT CCGCCACAAC |
| ATCGAGGACG GCAGCGTGCA GCTCGCCGAC CACTACCAGC AGAACACCCC CATCGGCGAC |
| GGCCCCGTGC TGCTGCCCGA CAACCACTAC CTGAGCACCC AGTCCGCCCT GAGCAAAGAC |
| CCCAACGAGA AGCGCGATCA CATGGTCCTG CTGGAGTTCG TGACCGCCGC CGGGATCACT |
| CTCGGCATGG ACGAGCTGTA CAAGTAAGTC GACGCTCGCT TCTTGCTGT CCAATTTCTA |
| TTAAAGGTTC CTTTGTTCCC TAAGTCCAAC TACTAAACTG GGGGATATTA TGAAGGGCCT |
| TGAGCATCTG GATTCTGCCT AAAAAAAAAA AAAAAAAAAA AAAAAAAAAA AAATCTAGAA |
| TGTTTTCTTG GGTTAATTGA GGCCTGAGTA TAAGGTGACT TATACTTGTA ATCTATCTAA |
| ACGGGGAACC TCTCTAGTAG ACAATCCCGT GCTAAATTGT AGGACTATCG ATTCGTAGCA |
| TAACCCCTTG GGGCCTCTAA ACGGGTCTTG AGGGGTTTTT TAAGCTTAT ATGGGGATAT |
| CCTCGAG |

FIGURE 7

| SEQ ID NO. 12: Gene 2CI – Expresses Circular mRNA containing IRES-GFP |
|---|
| AAGCTTTAAT ACGACTCACT ATAGGGCGGA TCCGGTTCTA CATAAAGCCT AACGATATCC |
| CTTTGGGAGT AGGTCAAGTG ACCGAAACGA TGACAACTTG TTTAACAAGT GGAGATATGT |
| CTGCTCTCAT GGTGACTGCA GCTGGTATAA TTCCGGGTAA GATAACGACC TTTCTGAACA |
| TAATGCTACC GTTTAATATT CTCGAGCGGG ATCAATTCCG CCCCCCCCCT AACGTTACTG |
| GCCGAAGCCG CTTGGAATAA GGCCGGTGTG CGTTTGTCTA TATGTTATTT TCCACCATAT |
| TGCGCCCGGA AACCTGGCCC TGTCTTCTTG ACGAGCATTC CTAGGGGTCT TTCCCCTCTC |
| GCCAAAGGAA TGCAAGGTCT GTTGAATGTC GTGAAGGAAG CAGTTCCTCT GGAAGCTTCT |
| TGAAGACAAA CAACGTCTGT AGCGACCCTT TGCAGGCAGC GGAACCCCCC ACCTGGCGAC |
| AGGTGCCTCT GCGGCCAAAA GCCACGTGTA TAAGATACAC CTGCAAAGGC GGCACAACCC |
| CAGTGCCACG TTGTGAGTTG GATAGTTGTG GAAAGAGTCA AATGGCTCTC CTCAAGCGTA |
| TTCAACAAGG GGCTGAAGGA TGCCCAGAAG GTACCCCATT GTATGGGATC TGATCTGGGG |
| CCTCGGTGCA CATGCTTTAC ATGTGTTTAG TCGAGGTTAA AAAAACGTCT AGGCCCCCCG |
| AACCACGGGG ACGTGGTTTT CCTTTGAAAA ACACGATGAT AATATGGCCA CAACCATGGT |
| GAGCAAGGGC GAGGAGCTGT TCACCGGGGT GGTGCCCATC CTGGTCGAGC TGGACGGCGA |
| CGTAAACGGC CACAAGTTCA GCGTGTCCGG CGAGGGCGAG GGCGATGCCA CCTACGGCAA |
| GCTGACCCTG AAGTTCATCT GCACCACCGG CAAGCTGCCC GTGCCCTGGC CCACCCTCGT |
| GACCACCCTG ACCTACGGCG TGCAGTGCTT CAGCCGCTAC CCCGACCACA TGAAGCAGCA |
| CGACTTCTTC AAGTCCGCCA TGCCCGAAGG CTACGTCCAG GAGCGCACCA TCTTCTTCAA |
| GGACGACGGC AACTACAAGA CCCGCGCCGA GGTGAAGTTC GAGGGCGACA CCCTGGTGAA |
| CCGCATCGAG CTGAAGGGCA TCGACTTCAA GGAGGACGGC AACATCCTGG GGCACAAGCT |
| GGAGTACAAC TACAACAGCC ACAACGTCTA TATCATGGCC GACAAGCAGA AGAACGGCAT |
| CAAGGTGAAC TTCAAGATCC GCCACAACAT CGAGGACGGC AGCGTGCAGC TCGCCGACCA |
| CTACCAGCAG AACACCCCCA TCGGCGACGG CCCCGTGCTG CTGCCCGACA ACCACTACCT |
| GAGCACCCAG TCCGCCCTGA GCAAAGACCC CAACGAGAAG CGCGATCACA TGGTCCTGCT |
| GGAGTTCGTG ACCGCCGCCG GGATCACTCT CGGCATGGAC GAGCTGTACA AGTAAGTCGA |
| CCTGCAGCCA AGCTTATCGA TAAAATAAAA GATTTTATTT AGTCTCCAGA AAAAGGGGGG |
| AATGAAAGAC CCCACCTGTA GGTTTGGCAA GCTAGCTTAA GTAACGCCAT TTTGCAAGGC |
| ATGGAAAATA CATAACTGAG AATAGAGAAG TTCAGATCAA GGTTAGGAAC AGAGAGACAG |
| CAGAATATGG GCCAAACAGG ATATCTGTGG TAAGCAGTTC CTGCCCCGGC TCAGGGCCAA |
| GAACAGATGG TCCCCAGATG CGGTCCCGCC CTCAGCAGTT TCTAGAATGT TTTCTTGGGT |
| TAATTGAGGC CTGAGTATAA GGTGACTTAT ACTTGTAATC TATCTAAACG GGGAACCTCT |
| CTAGTAGACA ATCCCGTGCT AAATTGTAGG ACTATCGATT CGTAGCATAA CCCCTTGGGG |
| CCTCTAAACG GGTCTTGAGG GGTTTTTTTA AGCTTATATG GGGATATCCT CGAG |

FIGURE 8

| SEQ ID NO. 13: Gene 3CIA – Expresses Circular mRNA containing IRES-GFP-beta globin 3'UTR-polyA sequence |
|---|
| AAGCTTTAAT ACGACTCACT ATAGGGCGGA TCCGGTTCTA CATAAAGCCT AACGATATCC CTTTGGGAGT AGGTCAAGTG ACCGAAACGA TGACAACTTG TTTAACAAGT GGAGATATGT CTGCTCTCAT GGTGACTGCA GCTGGTATAA TTCCGGGTAA GATAACGACC TTTCTGAACA TAATGCTACC GTTTAATATT CTCGAGCGGG ATCAATTCCG CCCCCCCCCT AACGTTACTG GCCGAAGCCG CTTGGAATAA GGCCGGTGTG CGTTTGTCTA TATGTTATTT TCCACCATAT TGCGCCCGGA AACCTGGCCC TGTCTTCTTG ACGAGCATTC CTAGGGGTCT TTCCCCTCTC GCCAAAGGAA TGCAAGGTCT GTTGAATGTC GTGAAGGAAG CAGTTCCTCT GGAAGCTTCT TGAAGACAAA CAACGTCTGT AGCGACCCTT TGCAGGCAGC GGAACCCCCC ACCTGGCGAC AGGTGCCTCT GCGGCCAAAA GCCACGTGTA TAAGATACAC CTGCAAAGGC GGCACAACCC CAGTGCCACG TTGTGAGTTG GATAGTTGTG GAAAGAGTCA AATGGCTCTC CTCAAGCGTA TTCAACAAGG GGCTGAAGGA TGCCCAGAAG GTACCCCATT GTATGGGATC TGATCTGGGG CCTCGGTGCA CATGCTTTAC ATGTGTTTAG TCGAGGTTAA AAAAACGTCT AGGCCCCCCG AACCACGGGG ACGTGGTTTT CCTTTGAAAA ACACGATGAT AATATGGCCA CAACCATGGT GAGCAAGGGC GAGGAGCTGT TCACCGGGGT GGTGCCCATC CTGGTCGAGC TGGACGGCGA CGTAAACGGC CACAAGTTCA GCGTGTCCGG CGAGGGCGAG GGCGATGCCA CCTACGGCAA GCTGACCCTG AAGTTCATCT GCACCACCGG CAAGCTGCCC GTGCCCTGGC CCACCCTCGT GACCACCCTG ACCTACGGCG TGCAGTGCTT CAGCCGCTAC CCCGACCACA TGAAGCAGCA CGACTTCTTC AAGTCCGCCA TGCCCGAAGG CTACGTCCAG GAGCGCACCA TCTTCTTCAA GGACGACGGC AACTACAAGA CCCGCGCCGA GGTGAAGTTC GAGGGCGACA CCCTGGTGAA CCGCATCGAG CTGAAGGGCA TCGACTTCAA GGAGGACGGC AACATCCTGG GGCACAAGCT GGAGTACAAC TACAACAGCC ACAACGTCTA TATCATGGCC GACAAGCAGA AGAACGGCAT CAAGGTGAAC TTCAAGATCC GCCACAACAT CGAGGACGGC AGCGTGCAGC TCGCCGACCA CTACCAGCAG AACACCCCCA TCGGCGACGG CCCCGTGCTG CTGCCCGACA ACCACTACCT GAGCACCCAG TCCGCCCTGA GCAAAGACCC CAACGAGAAG CGCGATCACA TGGTCCTGCT GGAGTTCGTG ACCGCCGCCG GGATCACTCT CGGCATGGAC GAGCTGTACA AGTAAGTCGA CGCTCGCTTT CTTGCTGTCC AATTTCTATT AAAGGTTCCT TGTTCCCTA AGTCCAACTA CTAAACTGGG GGATATTATG AAGGGCCTTG AGCATCTGGA TTCTGCCTAA AAAAAAAAAA AAAAAAAAAA AAAAAAAAAA ATCTAGAATG TTTTCTTGGG TTAATTGAGG CCTGAGTATA AGGTGACTTA TACTTGTAAT CTATCTAAAC GGGGAACCTC TCTAGTAGAC AATCCCGTGC TAAATTGTAG GACTATCGAT TCGTAGCATA ACCCCTTGGG GCCTCTAAAC GGGTCTTGAG GGGTTTTTTT AAGCTTATAT GGGGATATCC TCGAG |

FIGURE 9

| SEQ ID NO. 14: Gene 4EA – Expresses Circular mRNA containing eIF4E aptamer-beta globin 5'UTR-GFP- beta globin 3'UTR- polyA |
|---|
| AAGCTTTAAT ACGACTCACT ATAGGGCGGA TCCGGTTCTA CATAAAGCCT AACGATATCC<br>CTTTGGGAGT AGGTCAAGTG ACCGAAACGA TGACAACTTG TTTAACAAGT GGAGATATGT<br>CTGCTCTCAT GGTGACTGCA GCTGGTATAA TTCCGGGTAA GATAACGACC TTTCTGAACA<br>TAATGCTACC GTTTAATATT CTCGAGGGGA GACAAGAATA AACGCTCAAT GTTCAACCAG<br>AGTGAAACCA CTAACGGGTC AGAGCCCCTT CGACAGGAGG CTCACAACAG GCGAGCTCAC<br>ATTTGCTTCT GACACAACTG TGTTCACTAG CAACCTCAAA CAGACACCAT GGTGAGCAAG<br>GGCGAGGAGC TGTTCACCGG GGTGGTGCCC ATCCTGGTCG AGCTGGACGG CGACGTAAAC<br>GGCCACAAGT TCAGCGTGTC CGGCGAGGGC GAGGGCGATG CCACCTACGG CAAGCTGACC<br>CTGAAGTTCA TCTGCACCAC CGGCAAGCTG CCCGTGCCCT GGCCCACCCT CGTGACCACC<br>CTGACCTACG GCGTGCAGTG CTTCAGCCGC TACCCCGACC ACATGAAGCA GCACGACTTC<br>TTCAAGTCCG CCATGCCCGA AGGCTACGTC CAGGAGCGCA CCATCTTCTT CAAGGACGAC<br>GGCAACTACA AGACCCGCGC CGAGGTGAAG TTCGAGGGCG ACACCCTGGT GAACCGCATC<br>GAGCTGAAGG GCATCGACTT CAAGGAGGAC GGCAACATCC TGGGGCACAA GCTGGAGTAC<br>AACTACAACA GCCACAACGT CTATATCATG GCCGACAAGC AGAAGAACGG CATCAAGGTG<br>AACTTCAAGA TCCGCCACAA CATCGAGGAC GGCAGCGTGC AGCTCGCCGA CCACTACCAG<br>CAGAACACCC CCATCGGCGA CGGCCCCGTG CTGCTGCCCG ACAACCACTA CCTGAGCACC<br>CAGTCCGCCC TGAGCAAAGA CCCCAACGAG AAGCGCGATC ACATGGTCCT GCTGGAGTTC<br>GTGACCGCCG CCGGGATCAC TCTCGGCATG GACGAGCTGT ACAAGTAAGT CGACGCTCGC<br>TTTCTTGCTG TCCAATTTCT ATTAAAGGTT CCTTTGTTCC CTAAGTCCAA CTACTAAACT<br>GGGGGATATT ATGAAGGGCC TTGAGCATCT GGATTCTGCC TAAAAAAAAA AAAAAAAAAA<br>AAAAAAAAAA AAAATCTAGA ATGTTTTCTT GGGTTAATTG AGGCCTGAGT ATAAGGTGAC<br>TTATACTTGT AATCTATCTA AACGGGGAAC CTCTCTAGTA GACAATCCCG TGCTAAATTG<br>TAGGACTATC GATTCGTAGC ATAACCCCTT GGGGCCTCTA AACGGGTCTT GAGGGGTTTT<br>TTTAAGCTTA TATGGGATA TCCTCGAG |

FIGURE 10

| Circular RNA IRES-MCS-UTR-polyA Outline: HindIII site – T7 promoter — 5' Group I Intron circularization sequence – XhoI site – EMCV IRES — Multiple Cloning Site (SmaI, BamHI, XbaI, SalI, AccI, SmaI NotI, BglII, EcoRI, SacII, SalI) – 3' UTR beta globin – polyA tail – XbaI site – 3' Group I intron circularization sequence – ClaI site – T7 terminator - HindIII site |
|---|
| SEQ ID NO. 15: Circular RNA IRES-MCS-UTR-polyA = Vector allowing for Gene Insertion in multiple reading frames through a multiple cloning site in a Circular mRNA vector based on 3CIA (SEQ ID NO. 13). |

```
AAGCTTTAAT ACGACTCACT ATAGGGCGCG GTTCTACATA AAGCCTAACG ATATCCCTTT
GGGAGTAGGT CAAGTGACCG AAACGATGAC AACTTGTTTA ACAAGTGGAG ATATGTCTGC
TCTCATGGTG ACTGCAGCTG GTATAATTCC GGGTAAGATA ACGACCTTTC TGAACATAAT
GCTACCGTTT AATATTCTCG AGCGGGATCA ATTCCGCCCC CCCCCTAACG TTACTGGCCG
AAGCCGCTTG GAATAAGGCC GGTGTGCGTT TGTCTATATG TTATTTTCCA CCATATTGCG
CCCGGAAACC TGGCCCTGTC TTCTTGACGA GCATTCCTAG GGGTCTTTCC CCTCTCGCCA
AAGGAATGCA AGGTCTGTTG AATGTCGTGA AGGAAGCAGT TCCTCTGGAA GCTTCTTGAA
GACAAACAAC GTCTGTAGCG ACCCTTTGCA GGCAGCGGAA CCCCCCACCT GGCGACAGGT
GCCTCTGCGG CCAAAAGCCA CGTGTATAAG ATACACCTGC AAAGGCGGCA CAACCCCAGT
GCCACGTTGT GAGTTGGATA GTTGTGGAAA GAGTCAAATG GCTCTCCTCA AGCGTATTCA
ACAAGGGGCT GAAGGATGCC CAGAAGGTAC CCCATTGTAT GGGATCTGAT CTGGGGCCTC
GGTGCACATG CTTTACATGT GTTTAGTCGA GGTTAAAAAA ACGTCTAGGC CCCCCGAACC
ACGGGGACGT GGTTTTCCTT TGAAAAACAC GATGATAAGC TTGCCACAAC CCGGGATCCT
CTAGAGTCGA CCCGGGCGGC CGCTTCCCTA GATCTGAATT CCCGCGGTAA GTCGACGCTC
GCTTTCTTGC TGTCCAATTT CTATTAAAGG TTCCTTTGTT CCCTAAGTCC AACTACTAAA
CTGGGGGATA TTATGAAGGG CCTTGAGCAT CTGGATTCTG CCTAAAAAAA AAAAAAAAAA
AAAAAAAAAA AAAAAATAAT GTTTTCTTGG GTTAATTGAG GCCTGAGTAT AAGGTGACTT
ATACTTGTAA TCTATCTAAA CGGGGAACCT CTCTAGTAGA CAATCCCGTG CTAAATTGTA
GGACTATCGA TTCGTAGCAT AACCCCTTGG GGCCTCTAAA CGGGTCTTGA GGGGTTTTTT
TAAGCTTATA TGGGGATATC CTCGAG
```

INTRACELLULAR TRANSLATION OF CIRCULAR RNA

PRIOR RELATED APPLICATIONS

This application is a National Phase under 35 U.S.C. §371 of International Application PCT/US2014/37795, filed May 13, 2014, which claims priority to U.S. Provisional Application 61/823,709, filed May 15, 2013. Both applications are expressly incorporated by reference herein for all purposes.

FEDERALLY SPONSORED RESEARCH STATEMENT

Not applicable.

FIELD OF THE DISCLOSURE

The disclosure generally relates to a biologic product comprising a circular RNA that is capable of translation inside a eukaryotic cell. The invention describes novel combinations of RNA elements that facilitate the enhanced translation and expression of encoded polypeptides, and provides vectors for making circular mRNA, as well as various applications using the circular mRNA and/or vector.

BACKGROUND OF THE DISCLOSURE

"Gene therapy" is the use of DNA as an agent to treat disease. It derives its name from the idea that DNA can be used to supplement or alter genes within a patient's cells as a therapy to treat disease. The most common form of gene therapy involves using DNA that encodes a functional, therapeutic gene to replace a mutated, non-functional gene.

Although early clinical failures led many to dismiss gene therapy as over-hyped, clinical successes have now bolstered new optimism in the promise of gene therapy. These include successful treatment of patients with the retinal disease Leber's congenital amaurosis, X-linked severe combined immunodeficiency (SCID), adenosine deaminase SCID (ADA-SCID), adrenoleukodystrophy, chronic lymphocytic leukemia (CLL), acute lymphocytic leukemia (ALL), multiple myeloma and Parkinson's disease. These recent clinical successes have led to a renewed interest in gene therapy, with several articles in scientific and popular publications calling for continued investment in the field.

RNA is used in antisense and siRNA based therapies, but to date mRNA has not been used per se for gene therapy, even though the use of mRNA versus DNA in gene therapy offers potential advantages. For example, the protein encoded by the mRNA will be expressed in all cells, so selection of a promoter is not a problem. No insertional mutagenesis can occur, increasing the safety of the method, and the transient nature of expression is advantageous for many applications. The gene of interest can be easily expressed in dividing or non-dividing cells, as opposed to the limitations of DNA.

However, there are considerable technical difficulties to overcome before mRNA can be successfully used in various therapeutic methods.

For example, transfecting mRNA using lipids, electroporation, and other methods results in an inflammatory immune response mediated by Toll-like receptors recognizing the added RNA as foreign. This recognition leads to interferons being secreted, and if mRNA is attempted for repeated transfection, then ultimately cell death occurs via apoptosis.

A recent breakthrough allows the innate immune response to be avoided, thus providing a way of overcoming this first hurdle. The strategy incorporates modified nucleotides that cannot bind to toll-like receptors into the RNA, thus preventing the inflammatory immune response (e.g., U.S. Pat. No. 8,278,036, US20100047261, US20120322864). Thus, at least one challenge has been overcome in the challenges for implementing RNA-based therapeutic techniques.

Another difficulty has been the production of a complete and active mRNA via in vitro transcription. Further, the resulting mRNA must have all of the features needed for initiation and translation, and be able to effectively compete against endogenous mRNAs. Thus, the complete mRNA in the current art needs a 5' cap or cap analogue, 5' UTR, ORF, 3' UTR, and polyadenylation tail to mimic the standard mRNA molecule produced by eukaryotic cells. In some cases, a 5' cap is omitted and an IRES sequence utilized, but this is much more inefficient and reduces the half-life of the linear RNA molecule with no protection of the 5' terminus of RNA. Similarly, a polyadenylation tail can be omitted, but with reduced translation efficiency and half-life of the linear mRNA molecule.

Perhaps the biggest impediment, however, is the difficulty in handling mRNA. RNA has two adjacent pendant hydroxyls on the pentose ring of the terminal nucleotide, making it very susceptible to nucleophilic attack by bases or by ever-present RNAses in water and on most surfaces. RNAse-free reagents are used for the production of mRNA and its resultant storage, but even with such techniques, the extreme sensitivity to degradation presents considerably difficulty in implementing any RNA based technique. Yet another impediment is the short half-life of mRNA once inside the cell. Messenger RNA only affords transient expression inside cells, generally on the order of 6-12 hours.

It is well appreciated in the literature that circular RNA molecules have much longer half-lives than their linear counterparts, being naturally resistant to any exonuclease activity or nucleophilic attack. Thus, the use of circular RNA can solve both of these degradation issues. In fact, the half-life of circular RNA in vivo was estimated to be greater than 40 hours in *Xenopus* embryos. In the same system, linear mRNAs had a half-life of 6-8 hours. Even in *E. coli*, a circular RNA being actively translated was 4-6 times more stable than its linear counterpart due to resistance to RNase E activity.

It is also known that a Shine-Dalgarno sequence is necessary in prokaryotes for ribosome recruitment and can mediate recruit of ribosomes to any RNA molecule, whether linear or circular. However, circular RNA was originally thought to be unable to bind to eukaryotic ribosomes. Fortunately, Chen (1995) demonstrated that circular mRNA can bind eukaryotic ribosomes with the presence of an internal ribosome entry site (IRES).

Chen utilized a picornavirus IRES sequence for this purpose and demonstrated translation in an in vitro rabbit reticulocyte system. The primary goal of their strategy focused on the application of developing polymeric proteins through continuous translation around the circular RNA molecule. In order for this to occur, they eliminated the stop codon so that the ribosome would never be signaled to fall off the RNA molecule. In such constructs, only the IRES site and the coding sequence was present in the mRNA molecule, and other signals such as UTRs, polyA tracts, terminations sites and the like were missing.

In summary, for eukaryotes, a circular mRNA expression system has only been demonstrated in vitro in rabbit reticulocytes, a system that otherwise biases any level of background translation, even on a linear template without cap or IRES sequences. There was no data presented for the ability of a circular mRNA to translate in vivo inside a eukaryotic cell, and results in prokaryotes were disappointing. For application to an in vivo translation system inside the cell, more modifications are needed to circular mRNA in order to allow for its successful competition with native cellular mRNAs for translation initiation factors.

The Sarnow and Chen patent (U.S. Pat. No. 5,766,903) claims the insertion of an IRES into a circular RNA with a gene of interest. However, this patent fails to describe the necessity of other regulatory elements in the circular RNA molecule for in vivo translation. Indeed, there is no data demonstrating successful intracellular translation of circular mRNA in the patent or publication literature. There is no discussion of the insertion of a polyadenylation sequence, or a 3' UTR to function in synergy with the IRES element. Furthermore, novel IRES elements with improved translation in circular mRNA were not proposed.

Furthermore, there were almost no follow-up reports in the literature demonstrating the utility of circular mRNA, in vitro or in vivo. In one recent work, it was shown in a rabbit reticulocyte system in vitro that a circular mRNA template with the SP-A1 IRES could direct translation (Wang 2009). However, the translation efficiency of circular RNA in vitro was 15% that of an uncapped linear RNA with IRES. In the same experiment, a capped linear RNA had an activity that was 131% that of uncapped linear RNA, emphasizing how the rabbit reticulocyte system tends to bias uncapped transcripts toward levels of translation that are super-physiologic.

A variety of additional patents concern circular mRNA. However, these patents fail to provide evidence of actual in vivo translation of the circular mRNA molecule. Examples of prior art include U.S. Pat. No. 5,766,903, U.S. Pat. No. 6,210,931, U.S. Pat. No. 5,773,244 U.S. Pat. No. 5,580,859, US20100137407, U.S. Pat. No. 5,625,047, U.S. Pat. No. 5,712,128 US20110119782. Therefore, although possibly recognizing the potential of using circular mRNA for in vivo expression in eukaryotes, such applications were not in fact enabled.

Thus, what is needed in the art are methods of making and using circular mRNA where such molecules have been fully enabled and shown to work in in vivo or ex vivo eukaryotic systems.

SUMMARY OF THE DISCLOSURE

The present disclosure relates to a circular mRNA molecule that can effectively translate inside eukaryotic cells, as well as to methods of making and using same, and to the vectors used to produce circular mRNAs.

A preferred use includes the administration of circular mRNA molecules into mammalian cells or animals, e.g., for therapy or bioproduction of useful proteins. The method is advantageous in providing the production of a desired polypeptide inside eukaryotic cells with a longer half-life than linear RNA, due to resistance from ribonucleases and bases.

The circular mRNA can be transfected as is, or can be transfected in DNA vector form and transcribed in the cell, as desired. Cellular transcription can use added polymerases or nucleic acids encoding same, or preferably can use endogenous polymerases. We have demonstrated proof of concept herein with added T7 polymerases, but this is exemplary only, and more convenient cell based polymerases may be preferred.

The preferred half-life of a circular mRNA in a eukaryotic cell is at least 20 hrs, 30 hrs or even at least 40 hrs, as measured by either a hybridization or quantitative RT-PCR experiments.

A preferred embodiment of the invention consists of a circular mRNA molecule with an IRES, 5' UTR, coding sequence of interest, 3' UTR and polyadenylation sequence, in that order. It is well appreciated that many different combinations of these RNA elements with translation enhancing properties and synergy can be created. Such combinations include but are not limited to IRES-ORF-3' UTR-polyA, IRES-ORF-3' UTR, IRES-5' UTR-ORF-3' UTR, and the like.

One embodiment of the invention consists of a circular RNA molecule with modified RNA nucleotides. The possible modified ribonucleotide bases include 5-methylcytidine and pseudouridine. These nucleotides provide additional stability and resistance to immune activation.

Another embodiment of the invention consists of the in vitro transcription of a DNA template encoding the circular mRNA molecule of interest. Inverted intron self-splicing sequences at both ends of the RNA molecule facilitate the formation of circular RNA without any additional enzymes being needed.

An additional embodiment of the invention includes the production of circular mRNA inside the cell, which can be transcribed off a DNA template in the cytoplasm by a bacteriophage RNA polymerase, or in the nucleus by host RNA polymerase II.

One embodiment of the invention consists of the injection of circular mRNA into a human or animal, such that a polypeptide encoded by the circular mRNA molecule is expressed inside the organism. The polypeptide can either be found intracellularly or secreted.

In another embodiment of the invention, circular mRNA can be transfected inside cells in tissue culture to express desired polypeptides of interest. In particular, circular mRNA can express intracellular proteins and membrane proteins in the cells of interest.

The invention includes one or more of the following features, in all possible combinations thereof:

- A vector for making circular mRNA, said vector comprising the following elements operably connected to each other and arranged in the following sequence: a) an RNA polymerase promoter, b) a self circularizing intron 5' slice junction, c) an IRES, d) an optional 5' UTR, e) a multiple cloning insertion site for inserting an ORF into said vector, f) a 3' UTR, g) optionally a polyA tract, h) a self circularizing intron 3' slice junction, and i) an optional RNA polymerase terminator.
- A vector wherein the RNA polymerase promoter and terminator are from the T7 virus, T6 virus, SP6 virus, T3 virus, or T4 virus.
- A vector wherein the 3' UTRs are from human beta globin, human alpha globin *xenopus* beta globin, *xenopus* alpha globin, human prolactin, human GAP-43, human eEF1a1, human Tau, human TNF alpha, dengue virus, hantavirus small mRNA, bunyanavirus small mRNA, turnip yellow mosaic virus, hepatitis C virus, rubella virus, tobacco mosaic virus, human IL-8, human actin, human GAPDH, human tubulin, hibiscus chlorotic rinsgpot virus, woodchuck hepatitis virus post translationally regulated element, sindbis virus, turnip crinkle virus, tobacco etch virus, or Venezuelan equine encephalitis virus.
- A vector wherein the 5' UTRs are from human beta globin, *Xenopus laevis* beta globin, human alpha globin, *Xenopus laevis* alpha globin, rubella virus, tobacco mosaic virus, mouse Gtx, dengue virus, heat shock protein 70 kDa protein 1A, tobacco alcohol dehydrogenase, tobacco etch virus, turnip crinkle virus, or the adenovirus tripartite leader.

A vector wherein the polyA track is at least 30 nucleotides long or at least 60 nucleotides long.

A vector wherein the IRES is from Taura syndrome virus, *Triatoma* virus, Theiler's encephalomyelitis virus, Simian Virus 40, *Solenopsis invicta* virus 1, *Rhopalosiphum padi* virus, Reticuloendotheliosis virus, Human poliovirus 1, *Plautia stali* intestine virus, Kashmir bee virus, Human rhinovirus 2, Homalodisca coagulata virus-1, Human Immunodeficiency Virus type 1, Homalodisca coagulata virus-1, Himetobi P virus, Hepatitis C virus, Hepatitis A virus, Hepatitis GB virus, Foot and mouth disease virus, Human enterovirus 71, Equine rhinitis virus, Ectropis obliqua picorna-like virus, Encephalomyocarditis virus, *Drosophila* C Virus, Human coxsackievirus B3, Crucifer tobamovirus, Cricket paralysis virus, Bovine viral diarrhea virus 1, Black Queen Cell Virus, Aphid lethal paralysis virus, Avian encephalomyelitis virus, Acute bee paralysis virus, Hibiscus chlorotic ringspot virus, Classical swine fever virus, Human FGF2, Human SFTPA1, Human AML1/RUNX1, *Drosophila* antennapedia, Human AQP4, Human AT1R, Human BAG-1, Human BCL2, Human BiP, Human c-IAP1, Human c-myc, Human eIF4G, Mouse NDST4L, Human LEF1, Mouse HIF1 alpha, Human n.myc, Mouse Gtx, Human p27kip1, Human PDGF2/c-sis, Human p53, Human Pim-1, Mouse Rbm3, *Drosophila* reaper, Canine Scamper, *Drosophila* Ubx, Human UNR, Mouse UtrA, Human VEGF-A, Human XIAP, *Drosophila* hairless, *S. cerevisiae* TFIID, *S. cerevisiae* YAP1, WO0155369, tobacco etch virus, turnip crinkle virus, or an aptamer to eIF4G.

A vector including an RNA sequence that binds eIF4E when transcribed into the circular mRNA, functioning as an IRES element.

A vector wherein the RNA sequence binding to eIF4E is from Mouse histone H4, Human cyclin D1, Pea enation mosaic virus RNA2, *Panicum* Mosaic Virus, or an RNA aptamer to eIF4E.

A vector wherein the IRES is combined with a second IRES facilitating additional initiation factor recruitment, ribosome subunit binding, ribosome shunting, ribosome basepairing, or ribosome translocation.

A vector wherein in self-circularizing catalytic intron is a Group I intron or Group II Intron.

A vector comprising a nuclear transport element selected from Mason Pfizer Monkey Virus Constitutive Transport Element (CTE), 4E-SE element, woodchuck hepatitis virus post regulatory element, hepatitis b virus post regulatory element, or HIV rev response element.

A vector wherein said IRES comprises SEQ ID NO. 3.

A method of making circular mRNA, said method comprising adding ribonucleotide triphosphates, inorganic pyrophosphatase, RNase inhibitor, and an RNA polymerase to a vector herein described in appropriate reaction buffer, transcribing RNA from said vector, and allowing self-circularization of said transcribed RNA to produce circular mRNA.

A method as herein described, wherein said ribonucleotides including modified ribonucleotides m5C, m5U, m6A, s2U, Ψ, or 2'-O-methyl-U.

A method of making circular mRNA, said method comprising transfecting the vector herein described and a phage polymerase or nucleic acid encoding a phage polymerase into a eukaryotic cell, allowing for transcription of said vector inside the cell to produce transcribed RNA, and allowing self-circularization of said transcribed RNA to produce circular mRNA.

A method of making circular mRNA, said method comprising transfecting a vector herein described into a eukaryotic cell, wherein said vector is transcribed by a host cell RNA polymerase.

A circular mRNA made by any method or vector herein.

A circular mRNA with a half-life of at least 20 hrs in a eukaryotic cell or with a half-life of at least twice that of the same mRNA that is linear inside a eukaryotic cell.

A method of gene therapy, comprising introducing a circular mRNA into a patient in need thereof A method of gene therapy, comprising introducing a vector as described herein into a patient in need thereof A method of bioproducing a protein, comprising introducing a vector herein described into a eukaryotic cell or a mammal for production of a protein encoded by said ORF.

A method of bioproducing a protein, comprising introducing a circular mRNA into a eukaryotic cell or a mammal for production of a protein encoded by said ORF.

By "gene" herein what is a meant is a DNA molecule that includes at least promoter, ORF, and termination sequence and any other desired expression control sequences.

By "ORF" what is meant is an open reading frame, typically encoding a protein of interest.

By "in vivo" what is meant is translation of mRNA inside a cell, versus translation "in vitro" where a mixture of purified components included eukaryotic translation initiation factors, ribosomes, tRNAs charged with amino acids, and mRNA are mixed together without intact cells. "Ex vivo" means inside living cells that originated from a multicellular organism, but are now grown as cell cultures.

By "vector" or "cloning vector" what is meant is a small piece of DNA, taken from a virus, plasmid, or cell of a higher organism, that can be stably maintained in an organism, and into which a foreign DNA fragment can be inserted for cloning and/or expression purposes. A vector typically has an origin of replication, a selectable marker or reporter gene, such as antibiotic resistance or GFP, and usually contains a multiple cloning site. The term includes plasmid vectors, viral vectors, cosmids, bacterial artificial chromosomes (BACs), yeast artificial chromosomes (YACs), and the like.

In some embodiments the vector may also contain integration sequences, allowing for integration into a host genome, and such may be particularly preferred for cell based bioreactors because of increased stability.

An "expression vector" is a vector that also contains all of the sequences needed for transcription and translation of an ORF. These include a strong promoter, the correct translation initiation sequence such as a ribosomal binding site and start codon, a strong termination codon, and a transcription termination sequence. There are differences in the machinery for protein synthesis between prokaryotes and eukaryotes, therefore the expression vectors must have the elements for expression that is appropriate for the chosen host. For example, prokaryotes expression vectors would have a Shine-Dalgarno sequence at its translation initiation site for the binding of ribosomes, while eukaryotes expression vectors contains the Kozak consensus sequence.

A "multiple cloning site" or "MCS", also called a "polylinker," is a short segment of DNA which contains many (up to ~20) restriction sites and is a standard feature of engineered plasmids and other vectors. Restriction sites within an MCS are typically unique, occurring only once within a given plasmid, and can therefore be used to insert an ORF of interest into a vector. Furthermore, expression vectors are often designed so that the MCS can insert the ORF in the correct reading frame by choosing the correct insertion site, and/or the user can select the reading frame by choice of vectors, which are often available in all three frames.

"Aptamers" are oligonucleic acid or peptide molecules that bind to a specific target molecule. Aptamers are usually created by selecting them from a large random sequence pool, but natural aptamers also exist in riboswitches. Aptamers can be used for both basic research and clinical purposes as macromolecular drugs. Aptamers can be combined with ribozymes to self-cleave in the presence of their target molecule. These compound molecules have additional research, industrial and clinical applications.

More specifically, nucleic acid aptamers can be classified as DNA or RNA or XNA aptamers. They consist of (usually short) strands of oligonucleotides. Peptide aptamers consist of a short variable peptide domain, attached at both ends to a protein scaffold.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention, such as instructions for use, buffers, and the like.

| ABBREVIATION | TERM |
| --- | --- |
| GFP | Green fluorescent protein |
| ORF | Open reading frame |
| IRES | Internal ribosome entry site |
| UTR | Untranslated region |
| DAPI | 4',6-diamidino-2-phenylindole is a fluorescent stain that binds strongly to A-T rich regions in DNA. |
| HEK | Human embryonic kidney |
| IRES | Interal Ribosome Entry Site |
| CITE | Cap independent Translation Element |
| PEMV | Pea enation mosaic virus |
| 4E-SE | 4E sensitive element |
| EMCV | Encephalomyocarditis virus, a picornavirus |
| PFA | Paraformaldehyde |

BRIEF DESCRIPTION OF THE DRAWINGS

FIG. 4 shows SEQ ID NOs. 1-9. SEQ ID NO. 1: T7 RNA Polymerase Promoter (21 bp); SEQ ID NO. 2: 5' Group I Intron sequence (167 bp); SEQ ID NO. 3: eIF4E aptamer 1 sequence (86 bp); SEQ ID NO. 4: Human Beta Globin 5' UTR (50 bp); SEQ ID NO. 5: Human Beta Globin 3' UTR (133 bp); SEQ ID NO. 6: 3' Group I Intron sequence (107 bp); SEQ ID NO. 7: T7 RNA Polymerase Terminator (47 bp); SEQ ID NO. 8: Polyadenylation Sequence (33 bp); SEQ ID NO. 9: EMCV IRES (593 bp).

FIG. 5 shows SEQ ID NO. 10: pBSK-CR sequence=synthesized DNA sequence based on the outline provided in FIG. 5. Genes of Interest (GOI) can be cloned between NcoI and SalI and expressed as a circular mRNA with eIF4E aptamer-beta globin 5'UTR-GOI-beta globin 3'UTR-polyA.

FIG. 6 shows SEQ ID NO. 11: Gene 1LG-Expresses uncapped Linear mRNA containing IRES GFP.

FIG. 7 shows SEQ ID NO. 12: Gene 2CI-Expresses Circular mRNA containing IRES GFP.

FIG. 8 shows SEQ ID NO. 13: Gene 3CIA-Expresses Circular mRNA containing IRES GFP, beta globin 3'UTR and polyadenylation sequence.

FIG. 9 shows SEQ ID NO. 14: Gene 4EA-Expresses Circular mRNA containing eIF4E aptamer, beta globin 5'UTR, GFP, beta globin 3'UTR, and polyadenylation sequence.

FIG. 10. shows one exemplary vector sequence as SEQ ID NO. 15: Circular RNA IRES-MCS-UTR-polyA-Vector contains a multiple cloning site after an EMCV IRES and before beta globin 3'UTR and polyA sequence to allow for insertion of genes in multiple reading frames. Expression yields circular mRNA.

DETAILED DESCRIPTION

Figure 1:
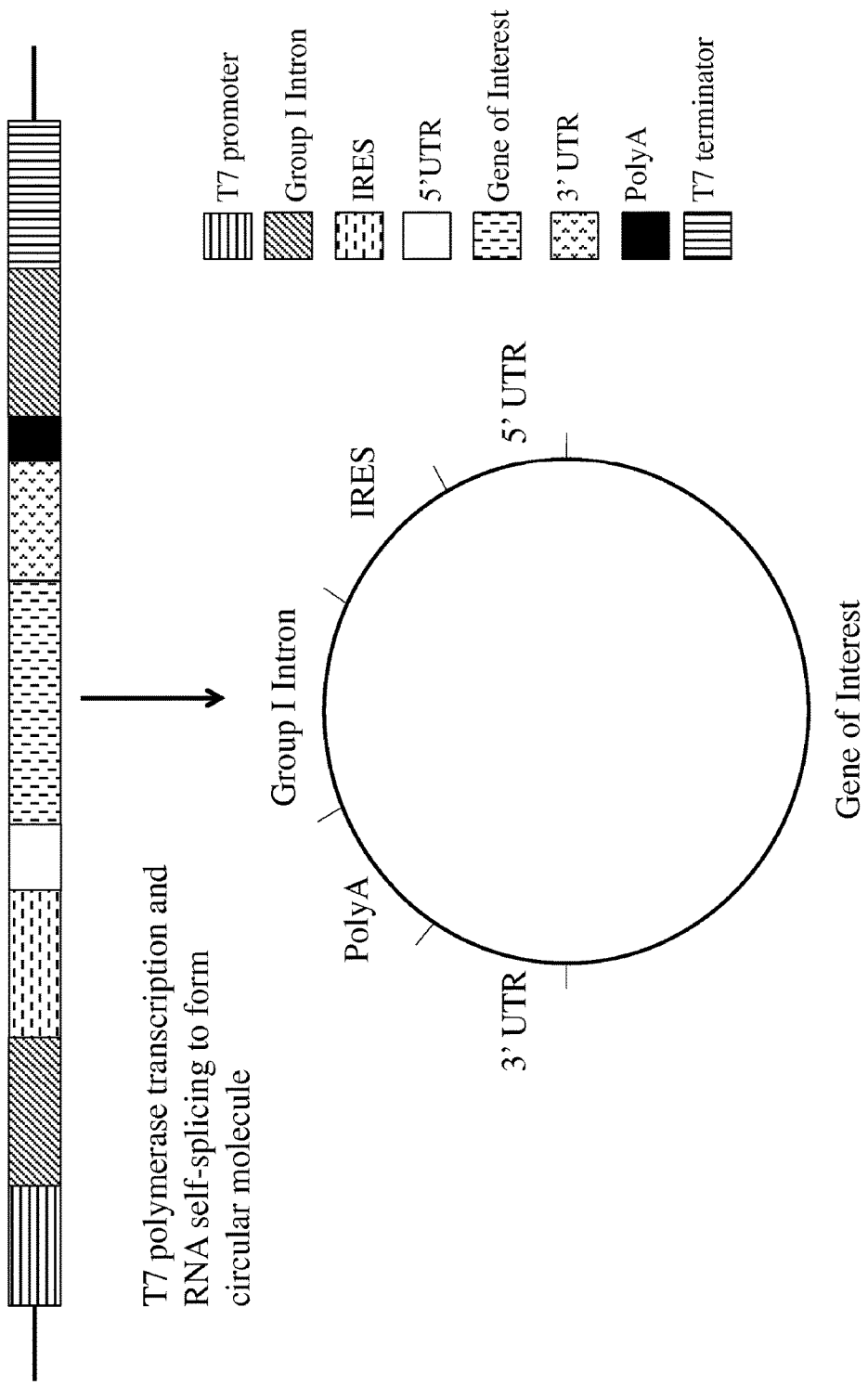
FIG. 1. Shows a vector designed to produce a circular mRNA molecule. The vector is shown with an ORF inserted thereinto, but before insertion a MCS would be shown instead.

The current disclosure describes circular mRNA molecules that can successfully translate inside mammalian cells, as well as methods of making same, vectors for making same, and methods of using either the vector or the circular mRNA.

The circular mRNA features additional regions beyond the IRES and ORF in order to help recruit ribosomes to the circular mRNA. The circular mRNA has an IRES site, an ORF for protein of interest, a 3'UTR, and an optional polyA track. In some embodiments of the invention, there can be both an IRES and a 5' UTR, depending upon how the IRES functions. Note that given the wide diversity of IRES sequences in nature, there will be a wide range of translational efficiencies when these IRES sequences are substituted in the proposed vector. In general, however, the invention will increase the efficiency of circular mRNA product regardless of the nature of the IRES in question because of the use of the polyA tail and 3' UTR elements, both of which help recruit ribosomes for translation.

In order for circular mRNAs to translate efficiently inside cells, they must compete in vivo against cellular mRNAs also recruiting the translation machinery. While IRES sequences have fewer translation initiation requirements, the canonical recruitment process via eIF4E still recruits ribosomes much more efficiently in a head to head comparison.

The present invention describes in addition to viral IRES sequences, an IRES sequence for circular mRNA that can recruit eIF4E itself.

In one embodiment of the invention, the IRES is an aptamer to eIF4E (SEQ ID NO. 3) with specificity for the face of the protein that binds the guanosine cap. This aptamer has never been used as an IRES before, and represents a novel aspect of the disclosure. The aptamer is able to bind to eIF4E and thereby the rest of the translation initiation complex, similar to cellular mRNA molecules. Helping translation initiation is the presence of the 3' UTR and polyA tail, meaning the circular mRNA in this embodiment of the invention can recruit ribosomes in almost the exact same way as cellular RNA. Cellular RNA circularizes by the way of a physical connection of PABP to eIF4G to eIF4E proteins, whereas the circular RNA in the invention is held together by a physical link.

Recruitment of eIF4E for cap-independent translation can be achieved by tethering eIF4E via a peptide tag to an RNA structure that specifically binds the tag. This suggests that if an RNA structure or aptamer or stem-loop could bind eIF4E directly, than cap-independent translation could be achieved. Indeed, this has been observed already for a plant virus, Pea enation mosaic virus (PEMV). Its RNA2 molecule contains a pseudoknot RNA structure that directly binds to plant eIF4E protein.

Certain eukaryotic transcripts are also able to recruit the eIF4E protein via RNA motifs in their 3' UTRs or coding sequences, acting independently of the cap binding mechanisms. This motif is called a 4E sensitive element, or 4E-SE. Examples of 4E-SEs are found in Mouse histone H4 mRNA and Human cyclin D1 mRNA. Their role in these mRNAs is to regulate nuclear localization and export, as well as modulating translation. For the purposes of a circular mRNA, it can easily be imagined that the 4E-SE could be used to similarly recruit eIF4E to the mRNA independent of cap and stimulate translation.

In another embodiment of the invention, the IRES is a 4E-SE element, taken from sequences in cellular mRNAs, which mediates direct binding to eIF4E. In this embodiment, a 5'UTR or IRES downstream of the 4E-SE may be added that promotes ribosome shunting as a way to stimulate non-canonical translation. An example would be the mouse Gtx 5'UTR or any viral or cellular IRES sequence.

As an alternative to using a 4E-SE sequence to bind eIF4E, an aptamer directed against the cap-binding pocket of eIF4E is proposed to be able to replicate the effects the normal guanosine cap in promoting translation. An example eIF4E aptamer sequence is given in SEQ ID NO. 3. As is known in the art, aptamers of many degenerate sequences can be generated against a given protein, and this is only one exemplary sequence.

In a similar fashion, novel IRESes could be developed that bind directly to eIF4G, skipping the necessary recruitment via eIF4E. An example of this strategy would be to develop aptamers against eIF4G that do not inhibit translation, but mediate strong binding to eIF4G.

Beyond utilizing novel IRES sequences, adding other RNA elements to the circular mRNA molecule allow for translation inside cells. It is readily recognized for example, that while the cap is an important structure for eukaryotic linear mRNA translation, the 5' UTR, 3' UTR and polyA tails also play important roles in translation.

The preferred embodiment of the invention contains a polyadenylation sequence within the circular RNA molecule of about 30-ribonucleotides of adenosine, which is able to bind to a single complex of human poly(A)-binding protein. This polyadenylation sequence would be located after the ORF, 3'UTR and before the splice site and termination signal.

Polyadenylation of mRNAs have been shown to increase the expression of viral IRES driven expression. The added polyA sequence in the circular mRNA might also function as a type of additional IRES site, as suggested by a report that a polyA 5' RNA leader could allow the bypass of initiation factors in mediating translation.

In addition to viral IRESes, cellular mRNAs can also have the translation efficiency of their IRES sequences increased with polyadenylation tails. The c-myc and BiP mRNA IRES activity could be enhanced though the addition of a polyA tail, even without intact eIF4G or PABP, factors which would normally mediate such an interaction.

In one embodiment of the invention, a pair of viral 5' and 3' UTRs may be utilized that naturally communicate with each other to mediate translation. The 5' and 3' UTRs of many viruses communicate through RNA-RNA or RNA-protein interactions to facilitate increased translation or regulation of translation. This suggests that optimizing the use of the said UTRs or by bringing the ends together permanently through circularization might lead to enhanced translation. One example of synergistic UTRs useful in the circular RNA invention is the pair of 5' and 3' UTRs from the dengue virus, which together possess IRES activity.

In the invention, the ability of 3' certain viral UTR sequences to augment or replace some of the canonical components of mRNA is also proposed. As an example, the 3'UTR of the Andes Hantavirus Small mRNA can functionally replace the polyA tail and can act in synergism with cap-dependent translation.

In another embodiment of the invention, a 5' UTR will be utilized that will facilitate the delivery of the ribosome to the first codon of the polypeptide to be translated. The mechanism of ribosomal tethering and delivery to downstream AUG codons would also be useful in circular mRNA molecules. This process is also referred to "ribosomal shunting." An example of a sequence that mediates shunting is an mRNA element from the 5' UTR of the Gtx homodomain mRNA, which basepairs to 18S rRNA, and the adenovirus tripartite leader.

While modified RNA nucleotides have received much attention for their resistance to nucleases in the setting of siRNA among other applications, modified RNA nucleotides produce only moderate improvements in translation efficiency and transcript half-life. Thus, circular RNA represents an improvement in the ability to achieve the longest transcript half-lives compared to all other methods today, while at the same time providing a much more robust and cheaper method of mRNA production requiring only the single RNA polymerase enzyme. This is compared to other mRNA in vitro product protocols in the prior art that require up to 3 enzyme reactions total (e.g., RNA polymerase, polyadenylase, and capping enzyme). Furthermore, RNA yields from transcription reactions mixed with cap analogue are generally 2-6 times lower than without, representing another production advantage for circular mRNA.

The circular mRNA described herein can also be produced in vivo inside the cell. There are two different embodiments for in vivo production of circular mRNA. In the first embodiment, DNA is delivered or integrated into nucleus. Transcription will be driven by a promoter recruiting a RNA polymerase II that is endogenous to that cell. Self-splicing would occur within the nucleus. Given that the 5' cap has been shown to be important for mRNA export, an alternative means may need to be added in order to increase circular mRNA export. An example is the Mason Pfizer Monkey Virus constitutive transport element (CTE), an RNA sequence which helps mediate non-canonical mRNA export.

The other means of in vivo circular mRNA generation would consist of transfecting linear or circular DNA containing an e.g., T7 promoter inside the cell, and adding e.g., T7. T7 polymerase protein could be transfected along with the plasmid DNA, whereafter in the cytoplasm it would bind the T7 promoter on the vector DNA and begin transcribing circular mRNA. In one embodiment of this method, the transcription cassette lacks a T7 terminator leading to continuous rolling circle transcription of RNA where T7 never dissociates from the DNA template.

In other embodiments, DNA encoding T7 DNA or even T7 mRNA could be added to the cell, allowing transcription and translation to produce the T7 inside the cell. Of course, T7 is exemplary only and any similar RNA polymerase could be used, such as T6, T4, T3, SP6, or RNA Polymerase I and the like.

The technologies required to produce circular RNA have been described in the literature previously. Commonly, group I self-splicing by a permuted intron-exon sequences from the T4 bacteriophage is used. This reaction can occur in prokaryotic cells, eukaryotic cells, or in vitro since it is catalyzed by RNA alone. However, a variety of different methods exist in that prior art concerning ways to synthesize circular RNA. It is understood that the proposed enhanced circular mRNA molecule could use any of these methods in its production (e.g., U.S. Pat. No. 6,210,931, U.S. Pat. No. 5,773,244).

Examples of group I intron self-splicing sequences include self-splicing permuted intron-exon sequences derived from T4 bacteriophage gene td. The intervening sequence (IVS) rRNA of Tetrahymena also contains an example of a Group I intron self splicing sequences. Given the widespread existence of group I and group II catalytic introns across nature, many possible sequences could be used for creating circular RNA.

Self-splicing occurs for rare introns that form a ribozyme, performing the functions of the spliceosome by RNA alone. There are three kinds of self-splicing introns, Group I, Group II and Group III. Group I and II introns perform splicing similar to the spliceosome without requiring any protein. This similarity suggests that Group I and II introns may be evolutionarily related to the spliceosome. Self-splicing may also be very ancient, and may have existed in an RNA world present before protein.

Cytoplasmic expression systems have been used before as an alternative to nuclear dependent transcription, or the transfection of mRNA itself. These systems rely on the co-transfection of a phage RNA polymerase (usually T7 DNA polymerase) with a DNA template. Sometimes, the T7 is expressed as a gene from a nuclear promoter, or the mRNA encoding T7 polymerase is transfected inside the cell. These provide alternatives to protein transfection of T7 polymerase. Furthermore, T7 polymerase could direct the synthesis of more T7 polymerase in certain systems, creating a self-sustaining autogene effect. Such autogene systems achieve unparalleled expression levels, and are only limited by the amount of triphosphate-ribonucleotides in the cytoplasm among other factors.

In another application of the invention, circular mRNAs could be generated continuously off a circular template, due to the highly processive nature of T7 RNA polymerase, which rarely falls off a DNA template during the elongation phase. T7 RNA polymerase can circle around plasmids many times if no proper termination sequence is provided. This has been shown in an shRNA system to produced a greatly increased yield of RNA product.

In an effort to mediate translation of RNA based technologies to clinical use, advances have been made in purifying mRNA on a large scale, eliminating double-stranded RNA impurities that can activate the innate immune system (e.g., EP2510099, EP2092064).

A related application distinct from circular mRNA molecules describes a circular RNA interference effector molecules (e.g., WO2010084371). Also, it has been recently published in the literature that human cells possess natural circular RNA molecules that appear to function as microRNA sponges. These circular RNA molecules were tested, however, and showed no translation activity, despite possessing exon sequences from proteins. In a slightly different application, the circular RNA molecules serve as substrates for Dicer and further processing to produce siRNA (e.g., EP2143792).

The following experiments are exemplary only and serve to provide proof of concept experiments for the invention generally. However, the invention and the claims should not be limited by the specific exemplars provided.

Vector Construction

A series of vectors were prepared to make circular mRNA matching the scheme outlined in FIG. 1. This template was then used to construct a series of different GFP encoding genes, which yield different types of mRNA molecules. The genes 1LG and 2CI produce linear mRNA molecules that exist in the prior art, while the genes 3CIA and 4CEA produce circular mRNA molecules that are novel to the current invention. As outlined below standard cloning procedures were utilized to produce the final vector DNA sequences.

The plasmid, pBSK-CR was prepared with a synthesized DNA sequence matching FIG. 5 (Seq. ID No. 10). Another plasmid, pIRES-GFP, containing the EMCV IRES followed by a GFP sequence was also obtained. The following cloning steps were undertaken to produce the vectors used to generate circular mRNAs herein:

Vector 1LG, which produces a linear, uncapped RNA molecule with IRES GFP-Beta Globin 3' UTR-polyA, was constructed by digestion with BamHI and SalI in both pIRES-GFP and pBSK-CR, followed by ligation of the IRES-GFP insert into the pBSK-CR sequence.

Vector 2CI, which produces a circular RNA molecule with IRES-GFP alone, was constructed by digestion of pIRES-GFP and pBSK-CR with XhoI and XbaI, followed by ligation of the IRES-GFP insert into the pBSK-CR sequence.

Vector 3CIA, which produces a circular RNA molecule with IRES-GFP-Beta Globin 3' UTR-polyA, was constructed by digestion of pIRES-GFP and pBSK-CR with XhoI and SalI, followed by ligation of the IRES-GFP insert into the pBSK-CR sequence.

Vector 4CEA, which produces a circular RNA molecule with eIF4E aptamer-beta globin 5' UTR-GFP-beta globin 3' UTR-polyA, was constructed by digestion of pBSK-CR and pIRES-GFP with NcoI and SalI, followed by ligation of the GFP insert into the pBSK-CR sequence.

Prior art plasmid pIRES-GFP produces a canonical linear capped mRNA with polyA tail that is produced inside the nucleus of a cell driven by a CMV promoter. This plasmid allows us to compare our novel circular mRNA with the expression of linear capped mRNAs and provides a direct comparison with the prior art. The relative mRNA levels produced will be different between the two systems given their different promoters, however.

Intracellular T7 Driven mRNA Expression

The purpose of this experiment was to generate mRNA inside the cell with T7 polymerase, eliminating variables of toxic effects of RNA during transfection, or the possible degradation of the mRNA by abundant RNases in the environment during experimental handling. The goal was to co-transfect plasmid DNA (combinations shown below) into HEK 293 cells together with active T7 RNA polymerase protein in a 24-well format, with four wells per condition. All amounts and volumes are given on a per well basis.

| Conditions | GFP expression | Expressed mRNA Sequences |
|---|---|---|
| pIRES-GFP + Lipofectamine | Positive Control | Linear capped IRES-GFP-polyA |
| 1LG + T7 + Lipofectamine | Positive Control | Linear uncapped IRES-GFP-3' UTR-polyA |
| 1LG + Lipofectamine | Negative Control | None (because no T7 added) |
| 2CI + T7 + Lipofectamine | Test condition | Circular IRES-GFP |
| 3CIA + T7 + Lipofectamine | Test condition | Circular IRES-GFP-3' UTR-polyA |
| 4CEA + T7 + Lipofectamine | Test condition | Circular eIF4E aptamer-5' UTR-GFP-3' UTR-polyA |

1. The day before transfection, HEK cells were trypsinized and counted. Cells were plated at $1.0 \times 10^5$ cells per well in 0.5 ml of complete growth medium.

2. 2 µg of DNA and 50 U of T7 RNA polymerase (NEB®) in 50 µl of serum-free OPTIMEM medium were combined, and incubated for 10 minutes at room temperature.

3. Pure lipofectamine (5 µl) was added to the plasmid/T7 RNA polymerase complex, the mixture incubated for 45 min, and then diluted to 200 µl with OPTIMEM medium.

4. After a further 30-minute incubation, 200 µl of the DNA-T7 polymerase-Lipofectamine reagent complexes were added directly to each well containing cells and mixed gently by rocking the plate back and forth. The DNA/protein/lipofectamine complexes do not have to be removed following transfection.

5. The cells are incubated at 37° C. in 5% $CO_2$ for 24 hours.

6. Pictures of the HEK cells were then taken using fluorescent microscope at 24 hours to detect GFP expression. In some experiments, the cells were fixed at 48 hours using 4% PFA, and then stained with DAPI to detect the outline of the nucleus of cells and improve GFP visualization. Localization of GFP could then be observed in reference to the position of the nucleus.

Figure 2:
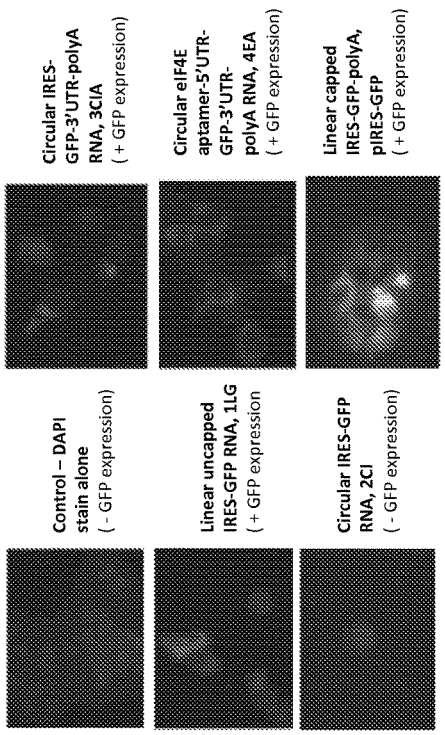
FIG. 2. Shows the GFP reporter protein imaging results from circular mRNA translation in HEK cells after T7 RNA polymerase driven expression.
Figure 3:
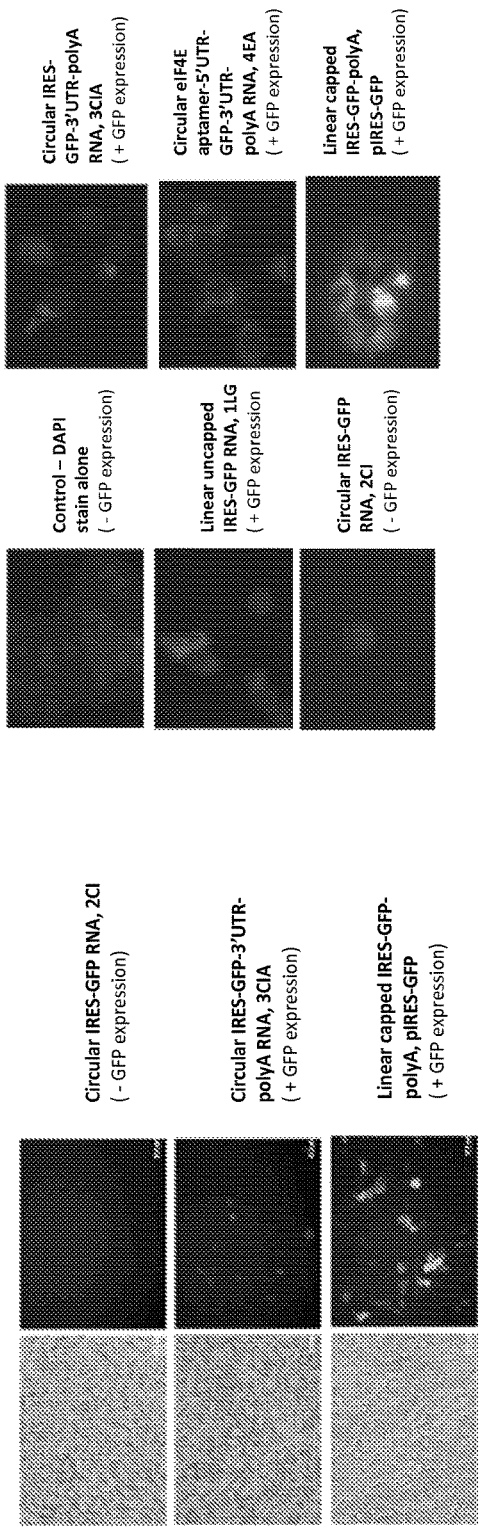
FIG. 3. Shows the GFP and DAPI (nuclear stain) imaging results from circular mRNA translation in HEK cells after T7 RNA polymerase driven expression.

The results of the experiment showed that the linear uncapped IRES-GFP-3' UTR-polyA expressed GFP (1LG), as has been observed in several systems. The 2CI circular mRNA, which matches the prior art of circular RNA with IRES and ORF elements only, failed to show GFP expression in repeated experiments when imaged during live cells (FIG. 2) or after cell fixation (FIG. 3). Thus, merely circularizing an RNA is not sufficient for eukaryotic expression in eukaryotic cells, even when the same mRNA is transcribable in linear form (not shown herein, but demonstrated in the prior art).

The 3CIA and 4CEA circular mRNAs of the invention exhibited distinct GFP expression, which was similar in GFP intensity to the linear uncapped 1LG mRNA.

| Conditions | GFP expression | Sequences | Results |
|---|---|---|---|
| pIRES-GFP + Lipofectamine | Positive Control | Linear capped IRES-GFP-polyA | +++ |
| 1LG + T7 + Lipofectamine | Positive Control | Linear uncapped IRES-GFP-3' UTR-polyA | ++ |
| 1LG + Lipofectamine | Negative Control | none | − |
| 2CI + T7 + Lipofectamine | Test condition | Circular IRES-GFP | − |
| 3CIA + T7 + Lipofectamine | Test condition | Circular IRES-GFP-3' UTR-polyA | ++ |
| 4CEA + T7 + Lipofectamine | Test condition | Circular eIF4E aptamer-5' UTR-GFP-3' UTR-polyA | ++ | mRNA Transcription and Transfection

The same vectors 1LG, 2CI, 3CIA, and 4EA from the previous experiment were used as templates for in vitro mRNA transcription. The process of in vitro mRNA transcription is well known in the field and consists of obtaining a DNA template with a phage promoter of short length followed by the gene of interest on the same sense strand. This DNA template is oftentimes linearized due to the high processivity of RNA polymerases, but can remain circular if a polymerase terminator sequence follows after the gene.

For the experiments herein, an in vitro mRNA transcription reaction was set up using the MEGAscript kit from Ambion®. A mixture of ribonucleotides, T7 polymerase and DNA template was added in a 20 µL reaction mixture. The reaction was allowed to proceed for 2 hours at 37° C. The mRNA transcripts were then purified using a standard lithium chloride protocol to remove excess ribonucleotides, DNA and protein.

The purified mRNA was then transfected into HEK 293 cells using Lipofectamine, as follows:

1. The day before transfection, HEK cells were trypsinized and counted. Cells were plated at $1.0 \times 10^5$ cells per well in 0.5 ml of complete growth medium.

2. 0.5-1 µg of RNA was added to 2.5 µL Lipofectamine 2000, the mixture was incubated for 45 min, and then diluted to 200 µl with OPTIMEM medium.

4. After a further 30-minute incubation, 200 µl of the mRNA-Lipofectamine Reagent complexes were added directly to each well containing cells and mixed by gently by rocking the plate back and forth. Complexes were not removed following transfection.

5. Cells were further incubated at 37° C. in 5% $CO_2$ for 24 hours.

6. Pictures of the HEK cells were taken using fluorescent microscope at 24 hours to detect GFP expression. In some experiments, the cells were fixed at 48 hours using 4% PFA, and then stain with DAPI to detect the outline of the nucleus of cells. Localization of GFP could then be observed in reference to the position of the nucleus.

The results of the mRNA transfection experiment matched the results of intracellular T7 driven mRNA expression, as expected. Linear uncapped IRES-GFP-3' UTR-polyA mRNA expressed GFP (1LG), as has been observed in several prior art systems. The 2CI circular mRNA, which matches the prior art of EMCV IRES and ORF alone (see U.S. Pat. No. 5,766,903), failed to show GFP expression in repeated experiments when imaged during live cells or after cell fixation. Thus, consistent with the above experiments, and IRES and ORF alone are insufficient for intracellular transcription of a circular mRNA. Furthermore, it is predicted to not be sufficient for live animal (in vivo) expression either.

The 3CIA and 4CEA circular mRNAs exhibited GFP expression, which was similar in GFP intensity to the linear uncapped 1LG mRNA.

| Conditions | GFP expression | Sequences | Results |
|---|---|---|---|
| pIRES-GFP + Lipofectamine | Positive Control | Linear capped IRES-GFP-polyA | +++ |
| 1LG + T7 + Lipofectamine | Positive Control | Linear IRES-GFP-3' UTR-polyA | ++ |
| 1LG + Lipofectamine | Negative Control | none | − |
| 2CI + T7 + Lipofectamine | Test condition | Circular IRES-GFP | − |
| 3CIA + T7 + Lipofectamine | Test condition | Circular IRES-GFP-3' UTR-polyA | ++ |
| 4CEA + T7 + Lipofectamine | Test condition | Circular eIF4E aptamer-5' UTR-GFP-3' UTR-polyA | ++ |

Conclusion

Using two different methods of circular mRNA production, it was observed for the first time that circular mRNA can be translated intracellularly in a eukaryotic cell in direct competition with host capped mRNAs. This is a significant finding that previous researchers were unable to accomplish. Furthermore, circular mRNAs that translate inside eukaryotic cells have not been found to exist in nature so far, and thus these results are unexpected. Indeed, while circular exons and introns are now appreciated to exist inside eukaryotic cells, evolution appears not to have selected for a circular mRNA capable translation by ribosomes. A summary of the experimental results is listed in the table below.

| Vector | Expressed RNA Molecule | Intracellular expression |
|---|---|---|
| pIRES-GFP | Linear capped IRES-GFP-polyA | Demonstrated in Previous Studies |
| 1LG | Linear IRES-GFP-3' UTR-polyA | Demonstrated in Current and Previous Studies |
| 2CI | Circular IRES-GFP | No Expression in Current Study |
| 3CIA | Circular IRES-GFP-3' UTR-polyA | Demonstrated in Current Study |
| 4CEA | Circular 4E aptamer-GFP-3'UTR-polyA | Demonstrated in Current Study |

The gene 2CI was constructed to produce a circular mRNA molecule that matches the prior art containing the same EMCV IRES and ORF construction (see U.S. Pat. No. 5,766,903). The 2CI gene thus serves as a comparison with the current invention, which contains multiple RNA translation enhancing elements. One observes that the 2CI circular mRNA encoding EMCV IRES-GFP alone fails to produce any discernable GFP expression both in live cell imaging and after fixation inside cells. This contrasts with its reported positive expression in an in vitro rabbit reticulocyte system (Chen & Sarnow, Science, 1995).

On the other hand, the circular mRNAs 3CIA and 4CEA produce expression patterns similar to the expression of linear uncapped mRNA 1LG. The linear mRNA 1LG containing uncapped EMCV IRES-GFP-beta globin 3'UTR-polyA is known in the literature to produce GFP after transfection, but we have demonstrated the first confirmed showing of expression of a circular version of the same mRNA.

The difference in GFP expression between circular mRNA in 2CI (no expression) and circular mRNA in 3CIA (expression) is remarkable, considering that the only additional sequences were the beta globin 3'UTR and polyadenylation sequence. This indicates that these added sequences were able to allow the EMCV IRES to effectively recruit ribosomes inside the cell, likely through helping recruit additional initiation factors to the IRES to increase its efficiency. For example, PABP binds to polyadenylation sequence and to eIF4G, which is a targeted protein by the EMCV IRES.

The present invention also describes for the first time the use of an eIF4E binding RNA sequence as an IRES-like element in recruiting ribosomes to circular RNA. So far, no mammalian viruses or cellular genes have been described that utilize eIF4E recruitment as an exclusive mechanism of ribosome recruitment. The demonstration of an eIF4E aptamer facilitating translation thus represents a novel finding for eukaryotic mRNA translation initiation.

Future experiments will explore optimization of circular mRNA genes using different combinations of IRES, 5' and 3' UTR, and length of polyadenylation sequences. The firefly luciferase gene will be utilized as the transfected ORF to allow for quantitative measurements of protein amounts produced after mRNA translation.

We also plan a future experiment to measure the half-life of our circular mRNA in eukaryotic cells, using quantitative RT-PCR and/or RNA purification and hybridization experiments. Based on the prior art teachings, we expect the half-life to be at least 2×, 3×, 4× or 5× higher than a control capped mRNA having a half-life of 10 hours Thus, we expect half-lives of at least 20 hrs, 30 hrs, 40 hrs or more.

Materials

Reduced Serum Media
Appropriate tissue culture plates and supplies
T7 Polymerase (New England Biosciences ®)
Lipofectamine 2000 (Invitrogen ®)
HEK 293 cells maintained in Dulbecco's Modified Eagle Medium (DMEM) medium (Invitrogen ®)
supplemented with 4 mM L-Glutamine (Invitrogen ®),
10% fetal bovine serum (Invitrogen ®). HEK
293 cells at 37° C. with 5% $CO_2$.
Plasmid DNA of interest
Lipofectamine 2000 Reagent (store at + 4° C. until ready to use)
Opti-MEM ®
MEGAscript kit (Ambion ®).

Each of the following references is incorporated by reference in its entirety for all purposes.
EP1083232 (Nicolette); US20080299662 (Ferrandez); US20080267873 US20100047261 (Hoerr); US20100137407 (Abe); US20100173356 (Lehmann); US20110104127 (Torzewski); US20110119782 US20110143397 (Dale); US20120322864 (Rossi); U.S. Pat. No. 5,580,859 U.S. Pat. No. 5,625,047 (Felgner); U.S. Pat. No. 5,712,128 (Been); U.S. Pat. No. 5,766,903 (Sarnow); U.S. Pat. No. 5,773,244 (Ares); U.S. Pat. No. 5,824,497 (Andrews); U.S. Pat. No. 6,210,931 (Feldstein); U.S. Pat. No. 8,192,984 U.S. Pat. No. 8,257,945

(Atebekov); U.S. Pat. No. 8,278,036 (Kariko); U.S. Pat. No. 8,383,340 (Ketterer); WO2010084371 (Plane).

Chen C. Y. & Sarnow P., Initiation of Protein Synthesis by the Eukaryotic Translational Apparatus on Circular RNAs. Science, New Series, 268(5209): 415-417 (1995).

Culjkovic B., et al., eIF4E promotes nuclear export of cyclin D1 mRNAs via an element in the 3' UTR., Journal of Cell Biology 169(2): 245-256 (2005).

De Gregorio E., et al., Tethered-function analysis reveals that eIF4E can recruit ribosomes independent of its binding to the cap structure. RNA 7:106-113 (2001).

Ford E. & Ares, M., Synthesis of circular RNA in bacteria and yeast using RNA cyclase ribozymes derived from a group I intron of phage T4. Proc. Nat. Acad. Sci. USA 91: 3117-3121 (1994).

Harland R. & Misher L., Stability of RNA in developing Xenopus embryos and identification of a destabilizing sequence in TFIIIA messenger RNA. Development 102: 837-852 (1988).

Konarska, M., et al., Binding of Ribosomes to Linear and Circular Forms of the 5'-Terminal Leader Fragment of Tobacco-Mosaic-Virus RNA. Eur. J. Biochem. 114: 221-227 (1981).

Mackie, G. A., Stabilization of Circular rpsT mRNA Demonstrates the 5-End Dependence of RNase E Action in Vivo, Journal Of Biological Chemistry 275: 33 (2000).

Mochizuki K., et al., High affinity RNA for mammalian initiation factor 4E interferes with mRNA-cap binding and inhibits translation, RNA 11: 77-89 (2005).

Perriman & Ares, Circular mRNA can direct translation of extremely long repeating-sequence proteins in vivo. RNA (1998) 4:1047-1054.

Perriman, R. Circular mRNA Encoding for Monomeric and Polymeric Green Fluorescent Protein. Methods in Molecular Biology 183:69-85 (2002).

Puttaraju M. & Been M. D., Circular Ribozymes Generated in *Escherichia coli* Using Group I Self-splicing Permuted Intron-Exon Sequences, Journal Of Biological Chemistry 271(42): 26081-26087 (1996).

Umekage, S. & Kikuchi Y., In vivo circular RNA production using a constitutive promoter for high-level expression. Journal of Bioscience and Bioengineering 108(4): 354-356 (2009).

Umekage, S. & Kikuchi Y., In vitro and in vivo production and purification of circular RNA aptamer. Journal of Biotechnology 139: 265-272 (2009).

Van Lieshout, J. F. T., et al., Ribozyme-mediated engineering of circular mRNA and its functional in vivo and in vitro translation (2007).

Wang Z., et al., The cap-binding translation initiation factor, eIF4E, binds a pseudoknot in a viral cap-independent translation element. Structure 19(6): 868-80 (2011).

Wang, G., et al., Cap-independent translation of human SP-A 5'-UTR variants: a double-loop structure and cis-element contribution, Am J Physiol Lung Cell Mol Physiol 296:L635-L647 (2009).

---

The invention claimed is:

1. A vector for making circular mRNA, said vector comprising the following elements operably connected to each other and arranged in the following sequence:
   a) an RNA polymerase promoter,
   b) a self circularizing intron 5' slice junction,
   c) an IRES,
   d) an optional 5' UTR,
   e) a multiple cloning insertion site for inserting an ORF into said vector,
   f) a 3' UTR,
   g) an optional polyA tract,
   h) a self circularizing intron 3' slice junction, and
   i) an optional RNA polymerase terminator,
   said vector allowing production of a circular mRNA that is able to compete against native cellular mRNAs for eukaryotic translation initiation machinery and that is translatable inside eukaryotic cells.

2. The vector of claim 1, wherein the RNA polymerase promoter and terminator are from a T7 virus, T6 virus, SP6 virus, T3 virus, or T4 virus.

3. The vector of claim 1, wherein the 3' UTR is from human beta globin, human alpha globin *xenopus* beta globin, *xenopus* alpha globin, human prolactin, human GAP-43, human eEF1a1, human Tau, human TNF alpha, dengue virus, hantavirus small mRNA, bunyanavirus small mRNA, turnip yellow mosaic virus, hepatitis C virus, rubella virus, tobacco mosaic virus, human IL-8, human actin, human GAPDH, human tubulin, hibiscus chlorotic rinsgpot virus, woodchuck hepatitis virus post translationally regulated element, sindbis virus, turnip crinkle virus, tobacco etch virus or Venezuelan equine encephalitis virus.

4. The vector of claim 1, wherein the 5' UTR is from human beta globin, *Xenopus laevis* beta globin, human alpha globin, *Xenopus laevis* alpha globin, rubella virus, tobacco mosaic virus, mouse Gtx, dengue virus, heat shock protein 70 kDa protein 1A, tobacco alcohol dehydrogenase, tobacco etch virus, turnip crinkle virus, or adenovirus tripartite leader.

5. The vector of claim 1, wherein the polyA track is at least 30 nucleotides long.

6. The vector of claim 1, wherein the polyA track is at least 60 nucleotides long.

7. The vector of claim 1, wherein the IRES is from Taura syndrome virus, *Triatoma* virus, Theiler's encephalomyelitis virus, simian virus 40, *Solenopsis invicta* virus 1, *Rhopalosiphum padi* virus, Reticuloendotheliosis virus, human poliovirus 1, *Plautia stali* intestine virus, Kashmir bee virus, Human rhinovirus 2, Homalodisca coagulata virus-1, Human Immunodeficiency Virus type 1, Himetobi P virus, Hepatitis C virus, Hepatitis A virus, Hepatitis GB virus, foot and mouth disease virus, Human enterovirus 71, Equine rhinitis virus, Ectropis obliqua picorna-like virus, Encephalomyocarditis virus, *Drosophila* C Virus, Human coxsackievirus B3, Crucifer tobamovirus, Cricket paralysis virus, Bovine viral diarrhea virus 1, Black Queen Cell Virus, Aphid lethal paralysis virus, Avian encephalomyelitis virus, Acute bee paralysis virus, Hibiscus chlorotic ringspot virus, Classical swine fever virus, Human FGF2, Human SFTPA1, Human AML1/RUNX1, *Drosophila* antennapedia, Human AQP4, Human AT1R, Human BAG-1, Human BCL2, Human BiP, Human c-IAP1, Human c-myc, Human eIF4G, Mouse NDST4L, Human LEF1, Mouse HIF1 alpha, Human N-myc, Mouse Gtx, Human p27kip1, Human PDGF2/c-sis, Human p53, Human Pim-1, Mouse Rbm3, *Drosophila* reaper, Canine Scamper, *Drosophila* Ubx, Human UNR, Mouse UtrA, Human VEGF-A, Human XIAP, *Drosophila* hairless, *S. cerevisiae* TFIID, *S. cerevisiae* YAP1, Human c-src, Human FGF-1, Simian picornavirus, Turnip crinkle virus, or an aptamer to eIF4G.

8. The vector of claim 1, further including an RNA sequence that binds eIF4E when transcribed into the circular mRNA.

9. The vector of claim 8, wherein the RNA sequence binding to eIF4E is from Mouse histone H4, Human cyclin D1, Pea enation mosaic virus RNA2, *Panicum* Mosaic Virus, or an RNA aptamer to eIF4E.

10. The vector of claim 1, wherein the IRES is combined with a second IRES facilitating additional initiation factor recruitment, ribosome subunit binding, ribosome shunting, ribosome base pairing, or ribosome translocation.

11. The vector of claim 1, wherein said self-circularizing catalytic intron is a Group I intron or Group II intron.

12. The vector of claim 1, further comprising a nuclear transport element selected from Mason Pfizer Monkey Virus Constitutive Transport Element (CTE), 4E-SE element, woodchuck hepatitis virus post regulatory element, hepatitis B virus post regulatory element, or HIV rev response element.

13. The vector of claim 1, said IRES comprising SEQ ID NO. 3.

14. A method of making circular mRNA, said method comprising adding ribonucleotide triphosphates, inorganic pyrophosphatase, RNase inhibitor, and an RNA polymerase to the vector of claim 1 in appropriate reaction buffer, transcribing RNA from said vector, and allowing self-circularization of said transcribed RNA to produce circular mRNA.

15. The method of claim 14, said ribonucleotides including modified ribonucleotides m5C, m5U, m6A, s2U, Ψ, or 2'-O-methyl-U.

16. A method of making circular mRNA, said method comprising transfecting the vector of claim 1 and a phage polymerase or nucleic acid encoding a phage polymerase into a eukaryotic cell, allowing for transcription of said vector inside the cell to produce transcribed RNA, and allowing self-circularization of said transcribed RNA to produce circular mRNA.

17. A method of making circular mRNA, said method comprising transfecting the vector of claim 1 into a eukaryotic cell, wherein said vector is transcribed by a host cell RNA polymerase.

* * * * *

SEQUENCE LISTING

```
<160> NUMBER OF SEQ ID NOS: 15

<210> SEQ ID NO 1
<211> LENGTH: 21
<212> TYPE: DNA
<213> ORGANISM: Artificial Sequence
<220> FEATURE:
<223> OTHER INFORMATION: Synthetic: T7 RNA Polymerase Promoter

<400> SEQUENCE: 1
taatacgact cactataggg c                                              21

<210> SEQ ID NO 2
<211> LENGTH: 167
<212> TYPE: DNA
<213> ORGANISM: Artificial Sequence
<220> FEATURE:
<223> OTHER INFORMATION: Synthetic: 5' Group I Intron sequence

<400> SEQUENCE: 2
ggttctacat aaagcctaac gatatccctt tgggagtagg tcaagtgacc gaaacgatga      60
caacttgttt aacaagtgga gatatgtctg ctctcatggt gactgcagct ggtataattc     120
cgggtaagat aacgaccttt ctgaacataa tgctaccgtt taatatt                  167

<210> SEQ ID NO 3
<211> LENGTH: 86
<212> TYPE: RNA
<213> ORGANISM: Artificial Sequence
<220> FEATURE:
<223> OTHER INFORMATION: Synthetic: eIF4E aptamer 1 sequence

<400> SEQUENCE: 3
gggagacaag aauaaacgcu caauguucaa ccagagugaa accacuaacg ggucagagcc      60
ccuucgacag gaggcucaca acaggc                                          86
```

<210> SEQ ID NO 4
<211> LENGTH: 50
<212> TYPE: DNA
<213> ORGANISM: Homo sapiens
<220> FEATURE:
<221> NAME/KEY: misc_feature
<223> OTHER INFORMATION: Human Beta Globin 5' UTR

<400> SEQUENCE: 4
acatttgctt ctgacacaac tgtgttcact agcaacctca aacagacacc         50

<210> SEQ ID NO 5
<211> LENGTH: 133
<212> TYPE: DNA
<213> ORGANISM: Homo sapiens
<220> FEATURE:
<221> NAME/KEY: misc_feature
<223> OTHER INFORMATION: Human Beta Globin 3' UTR

<400> SEQUENCE: 5
agctcgcttt cttgctgtcc aatttctatt aaaggttcct tgttccecta agtccaacta    60 ctaaactggg ggatattatg aagggccttg agcatctgga ttctgcctaa taaaaaacat   120
ttattttcat tgc                                                      133

<210> SEQ ID NO 6
<211> LENGTH: 107
<212> TYPE: DNA
<213> ORGANISM: Artificial Sequence
<220> FEATURE:
<223> OTHER INFORMATION: Synthetic: 3' Group I Intron sequence

<400> SEQUENCE: 6
atgttttctt gggttaattg aggcctgagt ataaggtgac ttatacttgt aatctatcta    60
aacggggaac ctctctagta gacaatcccg tgctaaattg taggact                 107

<210> SEQ ID NO 7
<211> LENGTH: 47
<212> TYPE: DNA
<213> ORGANISM: Artificial Sequence
<220> FEATURE:
<223> OTHER INFORMATION: Synthetic: T7 RNA Polymerase Terminator

<400> SEQUENCE: 7
tagcataacc ccttggggcc tctaaacggg tcttgagggg ttttttt                 47

<210> SEQ ID NO 8
<211> LENGTH: 33
<212> TYPE: DNA
<213> ORGANISM: Artificial Sequence
<220> FEATURE:
<223> OTHER INFORMATION: Synthetic: Polyadenylation Sequence

<400> SEQUENCE: 8
aaaaaaaaaa aaaaaaaaaa aaaaaaaaaa aaa                                33

<210> SEQ ID NO 9
<211> LENGTH: 593
<212> TYPE: DNA
<213> ORGANISM: Encephalomyocarditis virus
<220> FEATURE:
<221> NAME/KEY: misc_feature
<223> OTHER INFORMATION: Encephalomyocarditis virus (EMCV) IRES

<400> SEQUENCE: 9

| | | | | |
|---|---|---|---|---|
| gggcggctat | aggggcggct | cgagcgggat | caattccgcc | cccccccctaa cgttactggc | 60 |
| cgaagccgct | tggaataagg | ccggtgtgcg | tttgtctata | tgttattttc caccatattg | 120 |
| cgcccggaaa | cctggccctg | tcttcttgac | gagcattcct | aggggtcttt ccctctcgc | 180 |
| caaaggaatg | caaggtctgt | tgaatgtcgt | gaaggaagca | gttcctctgg aagcttcttg | 240 |
| aagacaaaca | acgtctgtag | cgacccttg | caggcagcgg | aaccccccac ctggcgacag | 300 |
| gtgcctctgc | ggccaaaagc | cacgtgtata | agatacacct | gcaaaggcgg cacaacccca | 360 |
| gtgccacgtt | gtgagttgga | tagttgtgga | aagagtcaaa | tggctctcct caagcgtatt | 420 |
| caacaagggg | ctgaaggatg | cccagaaggt | accccattgt | atgggatctg atctggggcc | 480 |
| tcggtgcaca | tgctttacat | gtgtttagtc | gaggttaaaa | aaacgtctag gccccccgaa | 540 |
| ccacggggac | gtggttttcc | tttgaaaaac | acgatgataa | tatggccaca acc | 593 |

<210> SEQ ID NO 10
<211> LENGTH: 689
<212> TYPE: DNA
<213> ORGANISM: Artificial Sequence
<220> FEATURE:
<223> OTHER INFORMATION: Synthetic: pBSK-CR sequence = synthesized DNA
sequence

<400> SEQUENCE: 10

| | | | | |
|---|---|---|---|---|
| aagctttaat | acgactcact | atagggcgga | tccggttcta | cataaagcct aacgatatcc | 60 |
| ctttgggagt | aggtcaagtg | accgaaacga | tgacaacttg | tttaacaagt ggagatatgt | 120 |
| ctgctctcat | ggtgactgca | gctggtataa | ttccgggtaa | gataacgacc tttctgaaca | 180 |
| taatgctacc | gtttaatatt | ctcgagggga | gacaagaata | aacgctcaat gttcaaccag | 240 |
| agtgaaacca | ctaacgggtc | agagccccct | cgacaggagg | ctcacaacag gcgagctcac | 300 |
| atttgcttct | gacacaactg | tgttcactag | caacctcaaa | cagacaccat ggtgcatctg | 360 |
| actcctgagt | cgacgctcgc | tttcttgctg | tccaatttct | attaaaggtt ctttgttcc | 420 |
| ctaagtccaa | ctactaaact | ggggatatt | atgaagggcc | ttgagcatct ggattctgcc | 480 |
| taaaaaaaa | aaaaaaaaaa | aaaaaaaaaa | aaaatctaga | atgttttctt gggttaattg | 540 |
| aggcctgagt | ataaggtgac | ttatacttgt | aatctatcta | aacggggaac ctctctagta | 600 |
| gacaatcccg | tgctaaattg | taggactatc | gattcgtagc | ataacccctt ggggcctcta | 660 |
| aacgggtctt | gagggtttt | tttaagctt | | | 689 |

<210> SEQ ID NO 11
<211> LENGTH: 1687
<212> TYPE: DNA
<213> ORGANISM: Artificial Sequence
<220> FEATURE:
<223> OTHER INFORMATION: Synthetic: Gene 1LG-Expresses uncapped Linear
mRNA containing IRES-GFP

<400> SEQUENCE: 11

| | | | | |
|---|---|---|---|---|
| aagctttaat | acgactcact | atagggcgga | tccggggcgg | ctatagggc ggctcgagcg | 60 |
| ggatcaattc | cgcccccccc | ctaacgttac | tggccgaagc | cgcttggaat aaggccggtg | 120 |
| tgcgtttgtc | tatatgttat | tttccaccat | attgcgcccg | gaaacctggc cctgtcttct | 180 |
| tgacgagcat | tcctaggggt | ctttcccctc | tcgccaaagg | aatgcaaggt ctgttgaatg | 240 |
| tcgtgaagga | agcagttcct | ctggaagctt | cttgaagaca | aacaacgtct gtagcgaccc | 300 |
| tttgcaggca | gcggaacccc | ccacctggcg | acaggtgcct | ctgcggccaa aagccacgtg | 360 |

| tataagatac | acctgcaaag | gcggcacaac | cccagtgcca | cgttgtgagt | tggatagttg | 420 |
| tggaaagagt | caaatggctc | tcctcaagcg | tattcaacaa | ggggctgaag | gatgcccaga | 480 |
| aggtacccca | ttgtatggga | tctgatctgg | ggcctcggtg | cacatgcttt | acatgtgttt | 540 |
| agtcgaggtt | aaaaaaacgt | ctaggccccc | cgaaccacgg | ggacgtggtt | ttcctttgaa | 600 |
| aaacacgatg | ataatatggc | cacaaccatg | gtgagcaagg | gcgaggagct | gttcaccggg | 660 |
| gtggtgccca | tcctggtcga | gctggacggc | gacgtaaacg | gccacaagtt | cagcgtgtcc | 720 |
| ggcgagggcg | agggcgatgc | cacctacggc | aagctgaccc | tgaagttcat | ctgcaccacc | 780 |
| ggcaagctgc | ccgtgccctg | gcccaccctc | gtgaccaccc | tgacctacgg | cgtgcagtgc | 840 |
| ttcagccgct | accccgacca | catgaagcag | cacgacttct | tcaagtccgc | catgcccgaa | 900 |
| ggctacgtcc | aggagcgcac | catcttcttc | aaggacgacg | gcaactacaa | gacccgcgcc | 960 |
| gaggtgaagt | tcgagggcga | caccctggtg | aaccgcatcg | agctgaaggg | catcgacttc | 1020 |
| aaggaggacg | gcaacatcct | ggggcacaag | ctggagtaca | actacaacag | ccacaacgtc | 1080 |
| tatatcatgg | ccgacaagca | gaagaacggc | atcaaggtga | acttcaagat | ccgccacaac | 1140 |
| atcgaggacg | gcagcgtgca | gctcgccgac | cactaccagc | agaacacccc | catcggcgac | 1200 |
| ggccccgtgc | tgctgcccga | caaccactac | ctgagcaccc | agtccgccct | gagcaaagac | 1260 |
| cccaacgaga | agcgcgatca | catggtcctg | ctggagttcg | tgaccgccgc | cgggatcact | 1320 |
| ctcggcatgg | acgagctgta | caagtaagtc | gacgctcgct | tcttgctgt | ccaatttcta | 1380 |
| ttaaaggttc | ctttgttccc | taagtccaac | tactaaactg | ggggatatta | tgaagggcct | 1440 |
| tgagcatctg | gattctgcct | aaaaaaaaaa | aaaaaaaaa | aaaaaaaaaa | aaatctagaa | 1500 |
| tgttttcttg | ggttaattga | ggcctgagta | taaggtgact | tatacttgta | atctatctaa | 1560 |
| acggggaacc | tctctagtag | acaatcccgt | gctaaattgt | aggactatcg | attcgtagca | 1620 |
| taacccettg | gggcctctaa | acgggtcttg | aggggttttt | ttaagcttat | atggggatat | 1680 |
| cctcgag | | | | | | 1687 |

<210> SEQ ID NO 12
<211> LENGTH: 1974
<212> TYPE: DNA
<213> ORGANISM: Artificial Sequence
<220> FEATURE:
<223> OTHER INFORMATION: Synthetic: Gene 2CI-Expresses Circular mRNA containing IRES-GFP

<400> SEQUENCE: 12

| aagctttaat | acgactcact | atagggcgga | tccggttcta | cataaagcct | aacgatatcc | 60 |
| ctttgggagt | aggtcaagtg | accgaaacga | tgacaacttg | tttaacaagt | ggagatatgt | 120 |
| ctgctctcat | ggtgactgca | gctggtataa | ttccgggtaa | gataacgacc | tttctgaaca | 180 |
| taatgctacc | gtttaatatt | ctcgagcggg | atcaattccg | cccccccct | aacgttactg | 240 |
| gccgaagccg | cttggaataa | ggccggtgtg | cgtttgtcta | tatgttattt | tccaccatat | 300 |
| tgcgcccgga | aacctggccc | tgtcttcttg | acgagcattc | ctaggggtct | ttcccctctc | 360 |
| gccaaaggaa | tgcaaggtct | gttgaatgtc | gtgaaggaag | cagttcctct | ggaagcttct | 420 |
| tgaagacaaa | caacgtctgt | agcgaccctt | gcaggcagc | ggaaccccc | acctggcgac | 480 |
| aggtgcctct | gcggccaaaa | gccacgtgta | taagatacac | ctgcaaaggc | ggcacaaccc | 540 |
| cagtgccacg | ttgtgagttg | gatagttgtg | gaaagagtca | atggctctc | tcaagcgta | 600 |
| ttcaacaagg | ggctgaagga | tgcccagaag | gtaccccatt | gtatgggatc | tgatctgggg | 660 |

```
cctcggtgca catgctttac atgtgtttag tcgaggttaa aaaaacgtct aggccccccg    720
aaccacgggg acgtggtttt cctttgaaaa acacgatgat aatatggcca caaccatggt    780
gagcaagggc gaggagctgt tcaccggggt ggtgcccatc ctggtcgagc tggacggcga    840
cgtaaacggc cacaagttca gcgtgtccgg cgagggcgag ggcgatgcca cctacggcaa    900
gctgaccctg aagttcatct gcaccaccgg caagctgccc gtgccctggc ccaccctcgt    960
gaccaccctg acctacggcg tgcagtgctt cagccgctac cccgaccaca tgaagcagca   1020
cgacttcttc aagtccgcca tgcccgaagg ctacgtccag gagcgcacca tcttcttcaa   1080
ggacgacggc aactacaaga cccgcgccga ggtgaagttc gagggcgaca ccctggtgaa   1140
ccgcatcgag ctgaagggca tcgacttcaa ggaggacggc aacatcctgg ggcacaagct   1200
ggagtacaac tacaacagcc acaacgtcta tatcatggcc gacaagcaga agaacggcat   1260
caaggtgaac ttcaagatcc gccacaacat cgaggacgga gcgtgcagc tcgccgacca   1320 ctaccagcag aacaccccca tcggcgacgg ccccgtgctg ctgcccgaca accactacct   1380
gagcacccag tccgccctga gcaaagaccc caacgagaag cgcgatcaca tggtcctgct   1440
ggagttcgtg accgccgccg ggatcactct cggcatggac gagctgtaca agtaagtcga   1500
cctgcagcca agcttatcga taaaataaaa gatttatttt agtctccaga aaaggggggg   1560
aatgaaagac cccacctgta ggtttggcaa gctagcttaa gtaacgccat tttgcaaggc   1620
atggaaaata cataactgag aatagagaag ttcagatcaa ggttaggaac agagagacag   1680
cagaatatgg gccaaacagg atatctgtgg taagcagttc ctgccccggc tcagggccaa   1740
gaacagatgt cccccagatg cggtcccgcc ctcagcagtt tctagaatgt tttcttgggt   1800
taattgaggc ctgagtataa ggtgacttat acttgtaatc tatctaaacg gggaacctct   1860
ctagtagaca atcccgtgct aaattgtagg actatcgatt cgtagcataa ccccttgggg   1920
cctctaaacg ggtcttgagg ggttttttta agcttatatg gggatatcct cgag         1974
```

<210> SEQ ID NO 13
<211> LENGTH: 1835
<212> TYPE: DNA
<213> ORGANISM: Artificial Sequence
<220> FEATURE:
<223> OTHER INFORMATION: Synthetic: Gene 3CIA-Expresses Circular mRNA
      containing IRES-GFP-beta globin 3'UTR-polyA sequence

<400> SEQUENCE: 13

```
aagctttaat acgactcact atagggcgga tccggttcta cataaagcct aacgatatcc     60
ctttgggagt aggtcaagtg accgaaacga tgacaacttg tttaacaagt ggagatatgt    120
ctgctctcat ggtgactgca gctggtataa ttccgggtaa gataacgacc tttctgaaca    180
taatgctacc gtttaatatt ctcgagcggg atcaattccg cccccccct aacgttactg     240 gccgaagccg cttggaataa ggccggtgtg cgtttgtcta tatgttattt tccaccatat    300
tgcgcccgga aacctggccc tgtcttcttg acgagcattc ctaggggtct ttcccctctc    360
gccaaaggaa tgcaaggtct gttgaatgtc gtgaaggaag cagttcctct ggaagcttct    420
tgaagacaaa caacgtctgt agcgacccct tgcaggcagc ggaaccccc acctggcgac    480 aggtgcctct gcggccaaaa gccacgtgta agatacac ctgcaaaggc ggcacaaccc    540
cagtgccacg ttgtgagttg gatagttgtg gaaagagtca aatggctctc ctcaagcgta    600
ttcaacaagg ggctgaagga tgcccagaag gtacccatt gtatgggatc tgatctgggg    660
cctcggtgca catgctttac atgtgtttag tcgaggttaa aaaaacgtct aggccccccg    720
```

```
aaccacgggg acgtggtttt cctttgaaaa acacgatgat aatatggcca caaccatggt      780
gagcaagggc gaggagctgt tcaccggggt ggtgcccatc ctggtcgagc tggacggcga      840
cgtaaacggc cacaagttca gcgtgtccgg cgagggcgag ggcgatgcca cctacggcaa      900
gctgaccctg aagttcatct gcaccaccgg caagctgccc gtgccctggc ccaccctcgt      960
gaccaccctg acctacggcg tgcagtgctt cagccgctac cccgaccaca tgaagcagca     1020
cgacttcttc aagtccgcca tgcccgaagg ctacgtccag gagcgcacca tcttcttcaa     1080
ggacgacggc aactacaaga cccgcgccga ggtgaagttc gagggcgaca ccctggtgaa     1140
ccgcatcgag ctgaagggca tcgacttcaa ggaggacggc aacatcctgg ggcacaagct     1200
ggagtacaac tacaacagcc acaacgtcta tatcatggcc gacaagcaga agaacggcat     1260
caaggtgaac ttcaagatcc gccacaacat cgaggacggc agcgtgcagc tcgccgacca     1320
ctaccagcag aacacccca tcggcgacgg ccccgtgctg ctgcccgaca ccactacct      1380 gagcacccag tccgccctga gcaaagaccc caacgagaag cgcgatcaca tggtcctgct     1440
ggagttcgtg accgccgccg ggatcactct cggcatggac gagctgtaca agtaagtcga     1500
cgctcgcttt cttgctgtcc aatttctatt aaaggttcct ttgttcccta agtccaacta     1560
ctaaactggg ggatattatg aagggccttg agcatctgga ttctgcctaa aaaaaaaaa     1620 aaaaaaaaa aaaaaaaaaa atctagaatg ttttcttggg ttaattgagg cctgagtata     1680
aggtgactta tacttgtaat ctatctaaac ggggaacctc tctagtagac aatcccgtgc     1740
taaattgtag gactatcgat tcgtagcata accccttggg gcctctaaac gggtcttgag     1800
gggttttttt aagcttatat ggggatatcc tcgag                                1835

<210> SEQ ID NO 14
<211> LENGTH: 1408
<212> TYPE: DNA
<213> ORGANISM: Artificial Sequence
<220> FEATURE:
<223> OTHER INFORMATION: Synthetic: Gene 4EA-Expresses Circular mRNA
      containing eIF4E aptamer-beta globin 5'UTR-GFP- beta globin
      3'UTR- polyA

<400> SEQUENCE: 14
aagctttaat acgactcact atagggcgga tccggttcta cataaagcct aacgatatcc       60
ctttgggagt aggtcaagtg accgaaacga tgacaacttg tttaacaagt ggagatatgt      120
ctgctctcat ggtgactgca gctggtataa ttccgggtaa gataacgacc tttctgaaca      180
taatgctacc gtttaatatt ctcgagggga gacaagaata aacgctcaat gttcaaccag      240
agtgaaacca ctaacgggtc agagccccttt cgacaggagg ctcacaacag gcgagctcac      300
atttgcttct gacacaactg tgttcactag caacctcaaa cagacaccat ggtgagcaag      360
ggcgaggagc tgttcaccgg ggtggtgccc atcctggtcg agctggacgg cgacgtaaac      420
ggccacaagt tcagcgtgtc cggcgagggc gagggcgatg ccacctacgg caagctgacc      480
ctgaagttca tctgcaccac cggcaagctg cccgtgccct ggcccaccct cgtgaccacc      540
ctgacctacg gcgtgcagtg cttcagccgc taccccgacc acatgaagca gcacgacttc      600
ttcaagtccg ccatgcccga aggctacgtc caggagcgca ccatcttctt caaggacgac      660
ggcaactaca agacccgcgc cgaggtgaag ttcgagggcg acaccctggt gaaccgcatc      720
gagctgaagg gcatcgactt caaggaggac ggcaacatcc tggggcacaa gctggagtac      780
aactacaaca gccacaacgt ctatatcatg gccgacaagc agaagaacgg catcaaggtg      840
aacttcaaga tccgccacaa catcgaggac ggcagcgtgc agctcgccga ccactaccag      900
```

-continued

```
cagaacaccc ccatcggcga cggccccgtg ctgctgcccg acaaccacta cctgagcacc      960
cagtccgccc tgagcaaaga ccccaacgag aagcgcgatc acatggtcct gctggagttc     1020
gtgaccgccg ccgggatcac tctcggcatg gacgagctgt acaagtaagt cgacgctcgc     1080
tttcttgctg tccaatttct attaaaggtt cctttgttcc ctaagtccaa ctactaaact     1140 ggggatatt atgaagggcc ttgagcatct ggattctgcc taaaaaaaa aaaaaaaaa       1200 aaaaaaaaa aaaatctaga atgttttctt gggttaattg aggcctgagt ataaggtgac     1260
ttatacttgt aatctatcta acggggaac ctctctagta gacaatcccg tgctaaattg      1320
taggactatc gattcgtagc ataacccctt ggggcctcta acgggtctt gagggttt       1380 tttaagctta tatggggata tcctcgag                                        1408
```

<210> SEQ ID NO 15
<211> LENGTH: 1166
<212> TYPE: DNA
<213> ORGANISM: Artificial Sequence
<220> FEATURE:
<223> OTHER INFORMATION: Synthetic: Circular RNA IRES-MCS-UTR-polyA

<400> SEQUENCE: 15

```
aagctttaat acgactcact atagggcgcg gttctacata aagcctaacg atatcccttt       60
gggagtaggt caagtgaccg aaacgatgac aacttgttta acaagtggag atatgtctgc      120
tctcatggtg actgcagctg gtataattcc gggtaagata acgaccttc tgaacataat       180 gctaccgttt aatattctcg agcgggatca attccgcccc cccctaacg ttactggccg      240 aagccgcttg gataaggcc ggtgtgcgtt tgtctatatg ttatttttcca ccatattgcg     300 cccggaaacc tggccctgtc ttcttgacga gcattcctag gggtcttcc cctctcgcca     360 aaggaatgca aggtctgttg aatgtcgtga aggaagcagt tcctctggaa gcttcttgaa    420
gacaaacaac gtctgtagcg acccttgca ggcagcggaa ccccccacct ggcgacaggt     480
gcctctgcgg ccaaaagcca cgtgtataag atacacctgc aaaggcggca caaccccagt   540
gccacgttgt gagttggata gttgtggaaa gagtcaaatg gctctcctca agcgtattca    600 acaagggct gaaggatgcc cagaaggtac cccattgtat gggatctgat ctggggcctc    660
ggtgcacatg ctttacatgt gtttagtcga ggttaaaaaa acgtctaggc ccccgaacc   720 acggggacgt ggttttcctt tgaaaaacac gatgataagc ttgccacaac ccgggatcct  780
ctagagtcga cccgggcggc cgcttcccta gatctgaatt cccgcggtaa gtcgacgctc    840
gctttcttgc tgtccaattt ctattaaagg ttcctttgtt ccctaagtcc aactactaaa    900 ctggggata ttatgaaggg ccttgagcat ctggattctg cctaaaaaaa aaaaaaaaa     960 aaaaaaaaa aaaaataat gttttcttgg gttaattgag gcctgagtat aaggtgactt   1020
atacttgtaa tctatctaaa cggggaacct ctctagtaga caatcccgtg ctaaattgta  1080
ggactatcga ttcgtagcat aaccccttgg ggcctctaaa cgggtcttga gggttttttt  1140
taagcttata tggggatatc ctcgag                                         1166
```

UNITED STATES PATENT AND TRADEMARK OFFICE
CERTIFICATE OF CORRECTION

PATENT NO. : 9,822,378 B2
APPLICATION NO. : 14/890799
DATED : November 21, 2017
INVENTOR(S) : Robert Kruse Page 1 of 1

It is certified that error appears in the above-identified patent and that said Letters Patent is hereby corrected as shown below:

In the Claims

In Column 31, Line 7, Claim 3 insert a -- , -- between human alpha goblin and xenopus beta globin In Column 31, Line 14, Claim 3 insert a -- - -- between post and translational (corrected from translationally)

In Column 31, Lines 18-19, the term xenopus should be lower case

Signed and Sealed this
Tenth Day of July, 2018

Andrei Iancu
*Director of the United States Patent and Trademark Office*